United States Patent
Chen et al.

(10) Patent No.: US 10,472,671 B2
(45) Date of Patent: Nov. 12, 2019

(54) WORKFLOW FOR DETECTION OF LIGANDS USING NUCLEIC ACIDS

(71) Applicant: LIFE TECHNOLOGIES CORPORATION, Carlsbad, CA (US)

(72) Inventors: Shiaw-Min Chen, Fremont, CA (US); Elana Swartzman, Alameda, CA (US); David Ruff, San Francisco, CA (US); Mark Shannon, San Francisco, CA (US); Julia Lu, San Jose, CA (US); Stephen Hendricks, Los Gatos, CA (US)

(73) Assignee: Life Technologies Corporation, Carlsbad, CA (US)

( * ) Notice: Subject to any disclaimer, the term of this patent is extended or adjusted under 35 U.S.C. 154(b) by 233 days.

(21) Appl. No.: 14/955,386

(22) Filed: Dec. 1, 2015

(65) Prior Publication Data
US 2016/0153035 A1 Jun. 2, 2016

Related U.S. Application Data

(63) Continuation of application No. 13/352,237, filed on Jan. 17, 2012, now abandoned.

(60) Provisional application No. 61/433,475, filed on Jan. 17, 2011.

(51) Int. Cl.
C12Q 1/68 (2018.01)
C12Q 1/6855 (2018.01)
C12Q 1/6804 (2018.01)

(52) U.S. Cl.
CPC ......... *C12Q 1/6855* (2013.01); *C12Q 1/6804* (2013.01)

(58) Field of Classification Search
CPC ...................................................... C12Q 1/68
See application file for complete search history.

(56) References Cited

U.S. PATENT DOCUMENTS

| | | | |
|---|---|---|---|
| 4,883,750 A | 11/1989 | Whiteley et al. | |
| 4,988,617 A | 1/1991 | Landegren et al. | |
| 5,426,180 A | 6/1995 | Kool | |
| 5,476,930 A | 12/1995 | Letsinger et al. | |
| 5,593,826 A | 1/1997 | Fung et al. | |
| 5,871,921 A | 2/1999 | Landegren et al. | |
| 5,925,517 A | 7/1999 | Tyagi et al. | |
| 6,037,130 A | 3/2000 | Tyagi et al. | |
| 6,872,521 B1 | 3/2005 | Boyce-Jacinto et al. | |
| 6,949,370 B1 * | 9/2005 | Barany ................... | C12N 9/93 435/183 |

(Continued)

FOREIGN PATENT DOCUMENTS

| | | |
|---|---|---|
| EP | 2665815 A1 | 11/2013 |
| WO | 1997/031256 | 8/1997 |

(Continued)

OTHER PUBLICATIONS

Kim et al. (Improvement of sensitivity and dynamic range in proximity ligation assays by asymmetric connector hybridization, Anal Chem. Aug. 15, 2010;82(16):6976-82).*

(Continued)

*Primary Examiner* — Aaron A Priest

(57) ABSTRACT

This application relates to methods for ligating oligonucleotides having complementarity to a target nucleic acid, and amplifying the ligated oligonucleotides, where ligation and amplification occur in the same reaction mixture.

17 Claims, 10 Drawing Sheets

Specification includes a Sequence Listing.

(56) References Cited

U.S. PATENT DOCUMENTS

| | | | |
|---|---|---|---|
| 7,255,994 | B2 | 8/2007 | Lao |
| 9,315,861 | B2 | 4/2016 | Hendricks et al. |
| 9,765,388 | B2 | 9/2017 | Hendricks et al. |
| 1,009,396 | A1 | 10/2018 | Hendricks et al. |
| 2002/0064779 | A1 | 5/2002 | Landegren et al. |
| 2002/0119464 | A1 | 8/2002 | McMillan |
| 2004/0110213 | A1 | 6/2004 | Namsaraev |
| 2008/0003571 | A1 | 1/2008 | McKernan |
| 2008/0032310 | A1 | 2/2008 | Shannon et al. |
| 2008/0293051 | A1* | 11/2008 | Levy ............... G01N 33/58 435/6.18 |
| 2009/0026082 | A1 | 1/2009 | Rothberg et al. |
| 2009/0162840 | A1* | 6/2009 | Fredriksson ......... C12Q 1/6804 435/6.12 |
| 2010/0081140 | A1 | 4/2010 | Church et al. |
| 2011/0008788 | A1* | 1/2011 | Paul ............... C12Q 1/6827 435/5 |
| 2011/0104785 | A1 | 5/2011 | Vaidyanathan et al. |
| 2012/0196294 | A1 | 8/2012 | Chen et al. |
| 2019/0024159 | A1 | 1/2019 | Hendricks et al. |

FOREIGN PATENT DOCUMENTS

| | | | | |
|---|---|---|---|---|
| WO | 2001/061037 | A1 | 8/2001 | |
| WO | 2001092579 | | 12/2001 | |
| WO | 2004/094456 | A2 | 11/2004 | |
| WO | 2005/123963 | A2 | 12/2005 | |
| WO | 2006/138527 | A2 | 12/2006 | |
| WO | 2007/107743 | A1 | 9/2007 | |
| WO | WO 2007107743 | A1 * | 9/2007 | ............ C12Q 1/682 |
| WO | 2007/121489 | | 10/2007 | |
| WO | 2008/016644 | A1 | 2/2008 | |
| WO | WO-2009149915 | A1 | 12/2009 | |
| WO | WO-2010111686 | A2 | 9/2010 | |
| WO | 2010/151842 | A2 | 12/2010 | |
| WO | 2012/099832 | A2 | 7/2012 | |
| WO | 2012/099896 | A2 | 7/2012 | |

OTHER PUBLICATIONS

Ho et al. (Characterization of an ATP-dependent DNA ligase encoded by Chlorella virus PBCV-1, Characterization of an ATP-dependent DNA ligase encoded by Chlorella virus PBCV-1).*
Univ. of Calgary (3'End Modifications, University Core DNA Services, attached, Jun. 14, 2010).*
Gustafsdottir et al. (Proximity ligation assays for sensitive and specific protein analyses, Anal Biochem. Oct. 1, 2005;345(1):2-9. Epub Feb. 7, 2005).*
Altschul, Stephen F, et al. , "Gapped BLAST and PSI-BLAST: a new generation of protein database search", Nucleic Acids Research, Sep. 1997, 3389-3402.
Barany, et al., "Genetic Disease Detection and DNA Amplification Using Cloned Thermostable Ligase", Proceedings of the National Academy of Sciences, 1991, 189-193.
Bi, W, et al., "CCR: a rapid and simple approach for mutation detection", Nucl. Acids Res., vol. 25(14), 1997, pp. 2949-2951.
Cheng, et al., "Characterization of an ATP-dependent DNA ligase encoded by Haemophilus influenzae", Nucleic Acids Research, Jan. 1, 1997, 1369-1374.
Creighton, et al., "Proteins: Structures and Molecular Principles", Apr. 1984, 1-8 pages.
Engler, M. J, et al., "DNA Ligases", The Enzymes, 15 , 1982 , 3-29.
EP1716644.4, EP Extended Search Report dated May 30, 2017, 1-14 pages.
Fasman, Gerald D., "UV Spectral Characteristics and Acidic Dissociation Constants of 280 Alkyl Bases. Nucleosides and Nucleotides", Practical Handbook of Biochemistry and Molecular Biology, 1989, pp. 385-394.
Fredriksson, et al., "Protein detection using proximity-dependent DNA ligation assays", Nature Biotechnology, May 1, 2002, 473-477.
Grossman, et al., "High-Density Multiplex Detection of Nucleic Acid Sequences: Oligonucleotide Ligation Assay and Sequence-Coded Separation", Nucleic Acids Research: vol. 22(21), 1994, 4527-4534.
Gullberg, et al., "Cytokine Detection by Antibody-based Proximity Ligation", Proceedings of National Academy of Science, Jun. 1, 2004, 8420-8424.
Higgins, N. Patrick, et al., DNA-Joining Enzymes: A Review , Methods in Enzymology, vol. 68, 1979, 50-71.
Ho, C. Kiong, et al., Characterization of an ATP-Dependent DNA Ligase Encoded by Chlorella Virus PBCV-1 , Journal of Virology, Vo. 71, No. 3, 1997, 1931-1937.
Holland, et al., "Detection of Specific Polymerase Chain Reaction Product by Utilizing the 5'->3' Exonuclease Activity of Thermus Aquaticus DNA Polymerase", Proceedings of the National Academy of Sciences, Aug. 15, 1991, 7276-7280.
Horspool, et al., "Efficient assembly of very short oligonucleotides using T4 DNA ligase", BMC Research Notes 201, 2010, 1-9.
Kim, et al., "Improvement of Sensitivity and Dynamic Range in Proximity Ligation Assays by Symmetric Connector Hibridization", Analytical Chemistry, Aug. 15, 2010, 6976-6982.
Landegren, et al., "A Ligase-Mediated Gene Detection Technique", Science 241, 1988, 1077-1080.
Landegren, U., "Ligation-based DNA Diagnostics", Bioessays, 15(11), 1993, 761-765.
Lohman, Gregory, et al., "Efficient DNA ligation in DNA-RNA hybrid helices by Chlorella virus DNA ligase", Nucleic Acids Research, 2014, 1831-1844.
McKernan, K, et al., "Sequence and structural variation in a human genome uncovered by short-read, massively parallel ligation sequencing using two-base encoding", Genome Res, 2009, 1527-1541.
Nakajima, Naoki , et al., "Mechanism of Amide Formation by Carbodiimide for Bioconjugation in Aqueous Media", Bioconjugate Chemistry, vol. 6, 1995, 123-130.
Nakatani, et al., "Substrate recognition and fidelity of strand joining by an archaeal DNA ligase", Eur. J. Biochem., 2002, 650-656.
Needleman, et al. , "A General Method Applicable to the Search for Similarities in the Amino Acid Sequence of Two Proteins", J. Mol. Biol., 1970, 443-453.
Odell, Mark, et al., "Analysis of the DNA joining repertoire of Chlorella virus DNA ligase and a new crystal structure of the ligase-adenylate intermediate", Nucl. Acids Res., 2003, 5090-5100.
PCT/US2012/021465, International Preliminary Report on Patentability dated Jul. 17, 2013, 11 pages.
PCT/US2012/021465, International Search Report and Written Opinion dated Aug. 27, 2012, 17 pages.
PCT/US2012/021465, Invitation to Pay Additional Fees dated Jun. 12, 2012, 8 pages.
Piserchio, et al., "Sequence-specific 1H N, 13C, and 15N backbone resonance assignments of the 34 kDa Paramecium bursaria Chlorella virus 1 (PBCV1) DNA ligase", Biomolecular NMR Assignments, Jun. 2009, 77-80.
Piserchio, et al., "Solution NMR Studies of Chlorella Virus DNA Ligase-adenylate", Journal of Molecular Biology, Jan. 15, 2010, 291-308.
Pritchard, Clare, et al., "Effects of base mismatches on joining of short oligodeoxynucleotides by DNA ligases", Nucleic Acids Research, Oxford University Press, Surrey, GB, 1997, 3403-3407.
Skobeltsyna, Larisa, et al., "Short Oligonucleotide Tandem Ligation Assay for Genotyping of Single-Nucleotide Polymorphisms in Y Chromosome", Molecular Biotechnology, 2010, 1-8.
Smith, Temple F, et al., "Comparison of biosequences", Advances in Applied Mathematics, vol. 2, No. 4, 1981, 482-489.
Sriskanda, et al., "Specificity And Fidelity Of Strand Joining By Chlorella Virus DNA Ligase", Nucleic Acids Research, 1998, 3536-3541.
Stratagene Catalog, "Gene Characterization Kits", 1988, p. 39.
Swartzman, et al., "Expanding applications of protein analysis using proximity ligation and aPCR", Methods: A Companion to Methods in Enzymology, Apr. 1, 2010, S23-S26.

(56) References Cited

OTHER PUBLICATIONS

Voelkerding, et al., "Next-Generation Sequencing:From Basic Research to Diagnostics", Clinical Chemistry, Apr. 2009, 641-658.

Xu, Y., et al., "High sequence fidelity in a non-enzymatic DNA autoligation reation", Nucl. Acids Res., vol. 27(3), 1999, pp. 875-881.

Zirvi, M., et al., "Ligase-Based Detection ofMononucleotide Repeat Sequences", Nuc Acids Res.vol. 27(24), 1999, pp. e40i-e40viii.

EP17185075.3, Extended European Search Report dated Nov. 14, 2017, 1-10.

Wiedmann, et al., "Ligase Chain Reaction (LCR)—Overview and Applications," PCR Methods and Applications CSH Laboratory Press, 1994, S51-S64.

Ahel et al. (The neurodegenerative disease protein aprataxin resolves abortive DNA ligation intermediates, Nature. Oct. 12, 2006;443 (7112):713-6. Epub Sep. 10, 2006).

Bornhorst et al. (Purification of Proteins Using Polyhistidine Affinity Tags, Ch. 16 in Methods Enzymol. 2000; 326: 245-254, available in PMC Jul. 25, 2010).

Brenner (Hint, Fhit and GalT: Function, Structure, Evolution and Mechanism of Three Branches of the Histidine Triad Superfamily of Nucleotide Hydrolases and Transferases, Biochemistry. Jul. 23, 2002; 41(29): 9003-9014).

Intl PCT/US2012/021585, "International Preliminary Report on Patentability", dated Jul. 17, 2013, 1-11.

Intl PCT/US2012/021585, "International Search Report and Written Opinion", dated Jul. 6, 2012, 1-18.

Odell and Shuman (Footprinting of Chlorella Virus DNA Ligase Bound at a Nick in Duplex DNA, The Journal of Biological Chemistry 274, 14032-14039, May 14, 1999).

PCT/US2012/066869, International Search Report and Written Opinion dated Feb. 8, 2013.

Rass, Ulrich et al., "Actions of Aprataxin in Multiple DNA Repair Pathways", Journal of Biological Chemistry, vol. 282, No. 13, 2007, 9469-9474.

Rass, Ulrich et al., "Molecular Mechanism of DNA Deadenylation by the Neurological Disease Protein Aprataxin", Journal of Biological Chemistry, vol. 283, No. 49, 2008, 33994-34001.

Zhang Z., et al., "A LDR-PCR approach for multiplex polymorphisms genotyping of severely degraded DNA with fragment sizes< 100 bp*," J. of Forensic Sciences 54 (6): 1304-09 (Year: 2009).

* cited by examiner

Asymmetrical and Symmetrical Oligo Splints

Asymmetrical (e.g., 3+6) splint

Symmetrical (e.g., 4+4) splint

WORKFLOW FOR DETECTION OF LIGANDS USING NUCLEIC ACIDS

CROSS-REFERENCE TO RELATED APPLICATION(S)

This application is a continuation of U.S. patent application Ser. No. 13/352,237 filed Jan. 17, 2012, which claims priority to U.S. Provisional Patent Application Ser. No. 61/433,475 filed Jan. 17, 2011, the disclosures of which are hereby incorporated herein by reference in their entirety as if set forth fully herein.

FIELD OF THE DISCLOSURE

This application relates to methods for ligating oligonucleotides having complementarity to a target nucleic acid, and amplifying the ligated oligonucleotides, where ligation and amplification occur in the same reaction mixture.

BACKGROUND OF THE DISCLOSURE

The correlation of gene and protein expression changes in biological systems has been hampered by the need for separate sample handling and analysis platforms for nucleic acids and proteins. In contrast to the simple, rapid, and flexible workflow of quantitative PCR (qPCR) methods, which enable characterization of several classes of nucleic acid biomarkers (e.g., DNA, mRNA, and microRNAs), protein analysis methods such as Western blotting are cumbersome, laborious, and much less quantitative. Proximity Ligation Assays (PLAs) have been shown to eliminate some of these problems. However, improvements to PLAs are desired by those of skill in the art.

Typical or conventional PLAs usually involve at least three or four steps. The first step is typically the binding of first and second probes (e.g., antibody probes) to a ligand (e.g., a protein of interest) such that the probes are in close proximity to another. Each of the probes typically contain an oligonucleotide. The oligonucleotides are brought into proximity to one another with the binding of the probes and, in the second step, are then ligated to one another (e.g., the ligation event). The ligated oligonucleotides may then be amplified and detected to determine the presence of the ligand with a test sample (e.g., a biological sample). This step is typically accomplished by adding ligation components, such as ligase, adenosine triphosphate (ATP) and buffer-salt mixture, to the binding reaction. In the third step, the ligase is typically then deactivated (e.g., by protease digestion) to prevent any further ligation of unbound oligonucleotides. In the fourth step, the reaction mixture is transferred to a real-time polymerase chain reaction (PCR) mixture and the quantity of the amplified product determined by quantitative PCR (qPCR). As described below, it has been surprisingly found that the third step (ligase digestion) may be eliminated, thereby allowing ligation and amplification to occur in the same reaction mixture without inactivation of the ligase. These and other features and advantages of the methods described herein will be apparent to the skilled artisan from this disclosure.

SUMMARY OF THE DISCLOSURE

Provided herein are methods for ligating and amplifying oligonucleotides. In some embodiments, the oligonucleotides are attached to ligand-specific probes, and amplification of the oligonucleotides indicates that the probes have bound a ligand in the sample. In one embodiment, a method for ligating at least two oligonucleotides to produce a ligated oligonucleotide and amplifying the ligated oligonucleotide, wherein ligation and amplification occur in a single reaction mixture (e.g., that may be considered undiluted) is provided. In some embodiments, a third oligonucleotide may be used to bridge the at least two oligonucleotides that are bound to the probes. In certain embodiments, the method may comprise detecting a ligand in a test sample (e.g., a biological sample) comprising contacting the protein with at least a first and second probe, each probe having binding specificity for the protein and being adjoined to at least one type of oligonucleotide, the oligonucleotides on the first and second probes, respectively, being at least partially complementary to one another; ligating the oligonucleotides on the first and second probes to one another using a ligase to produce a target nucleic acid and amplifying the target nucleic acid; and, detecting the amplified target nucleic acid. For instance, the method may comprise detecting a protein in a test sample, the method comprising contacting the protein with at least two probes having binding specificity therewith, each of the two agents comprising at least one oligonucleotide; ligating the oligonucleotides to produce a ligated oligonucleotide and amplifying the ligated oligonucleotide in a single reaction mixture; and, detecting amplification of the ligated oligonucleotide. In some embodiments, one or more of the probes is an antibody. In certain embodiments, at least one of the oligonucleotides comprises at least three nucleotides. Some embodiments provide for the oligonucleotide being ligated using a small footprint ligase, which may be contacted with adenosine triphosphate prior to use. Any type of amplification procedure may be used such as, without limitation, polymerase chain reaction (PCR) (e.g., quantitative PCR (qPCR)). In some embodiments, it may be beneficial to inactivate the ligase prior to amplification (e.g., using a protease). Other embodiments of the methods described herein will be apparent to the skilled artisan from the disclosure provided herein.

BRIEF DESCRIPTION OF THE DRAWINGS

The skilled artisan will understand that the drawings described below are for illustration purposes only. The drawings are not intended to limit the scope of the present teachings in any way.

FIG. 3B—A schematic diagram of an exemplary improved PLA workflow (as disclosed herein).

Figure 4A:
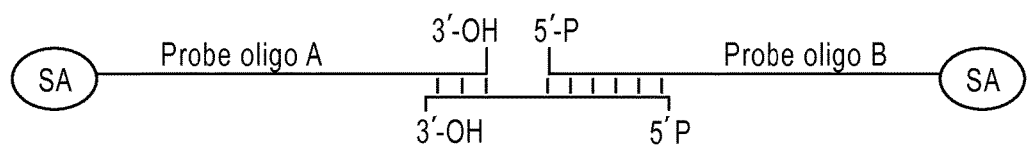
Figure 4B:
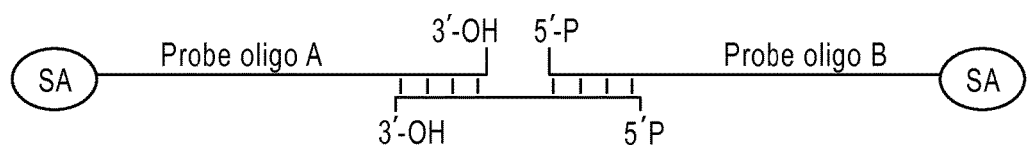

A schematic diagram of exemplary FIG. 4A—asymmetrical (e.g., 3+6) and FIG. 4B—symmetrical (e.g., 4+4) oligonucleotide splints ("connectors").

Figure 5:
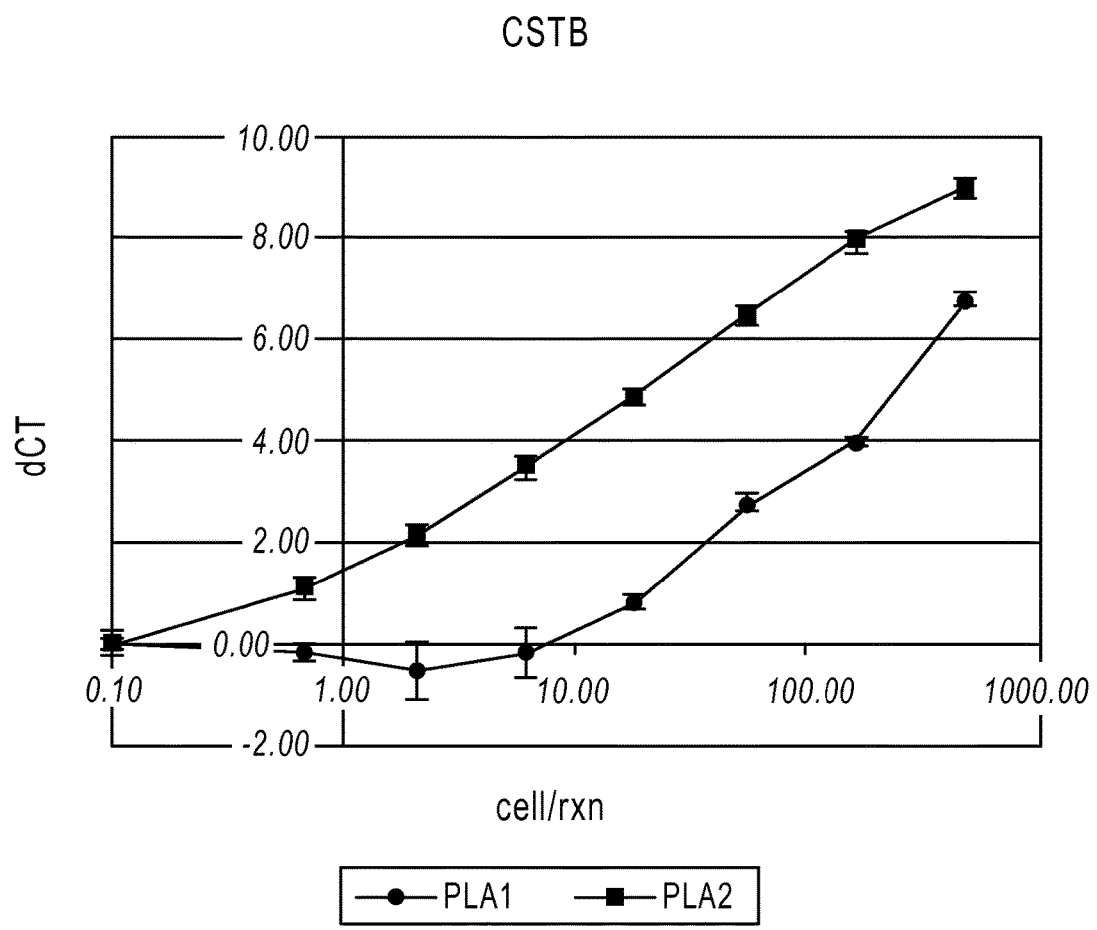

FIG. 5. Comparison of a typical or conventional PLA process (PLA1) and the improved process (PLA2) (dCT data shown).

Figure 6:
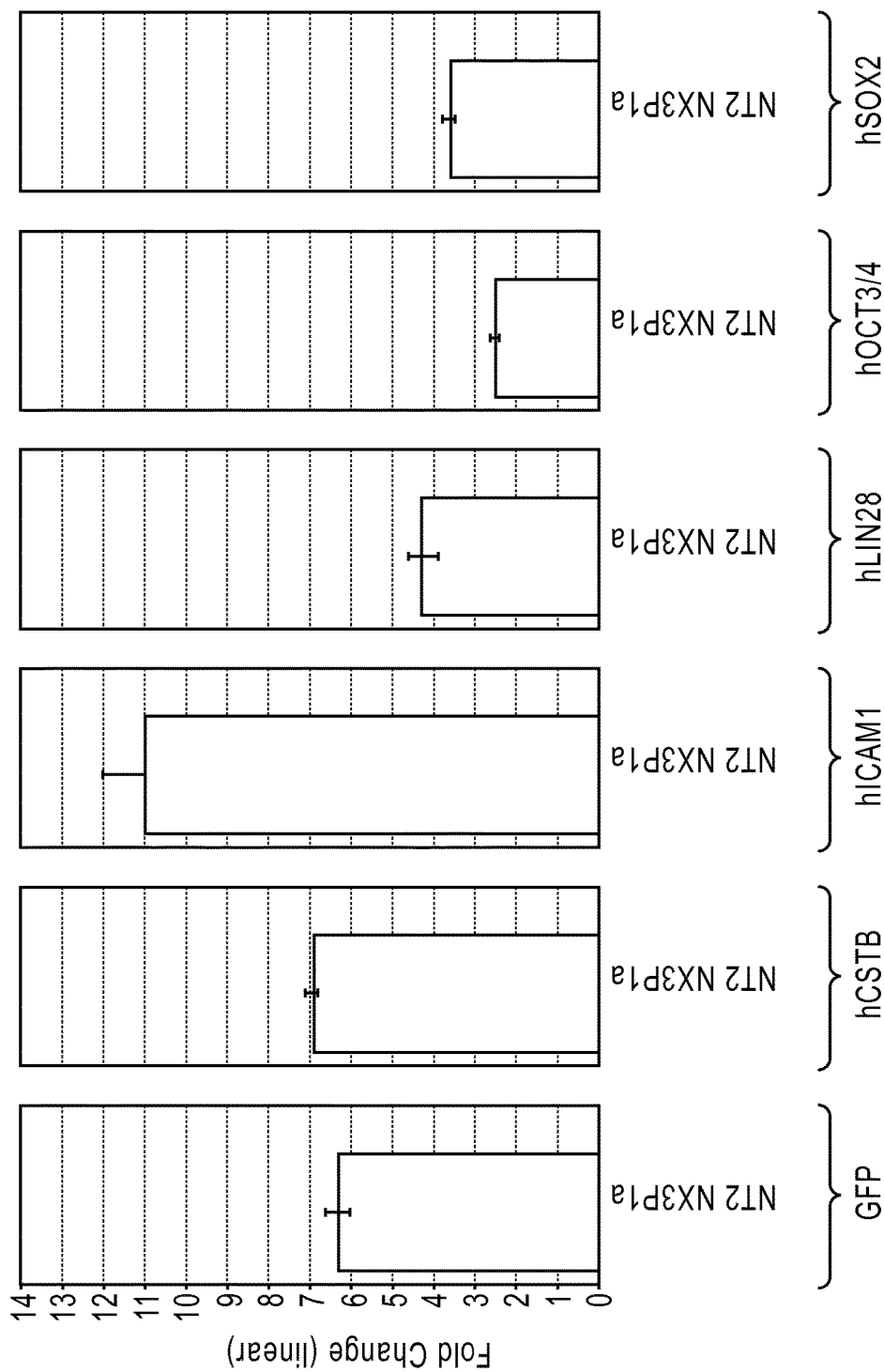

FIG. 6. Use of the improved PLA process with various target nucleic acids.

Figure 7:
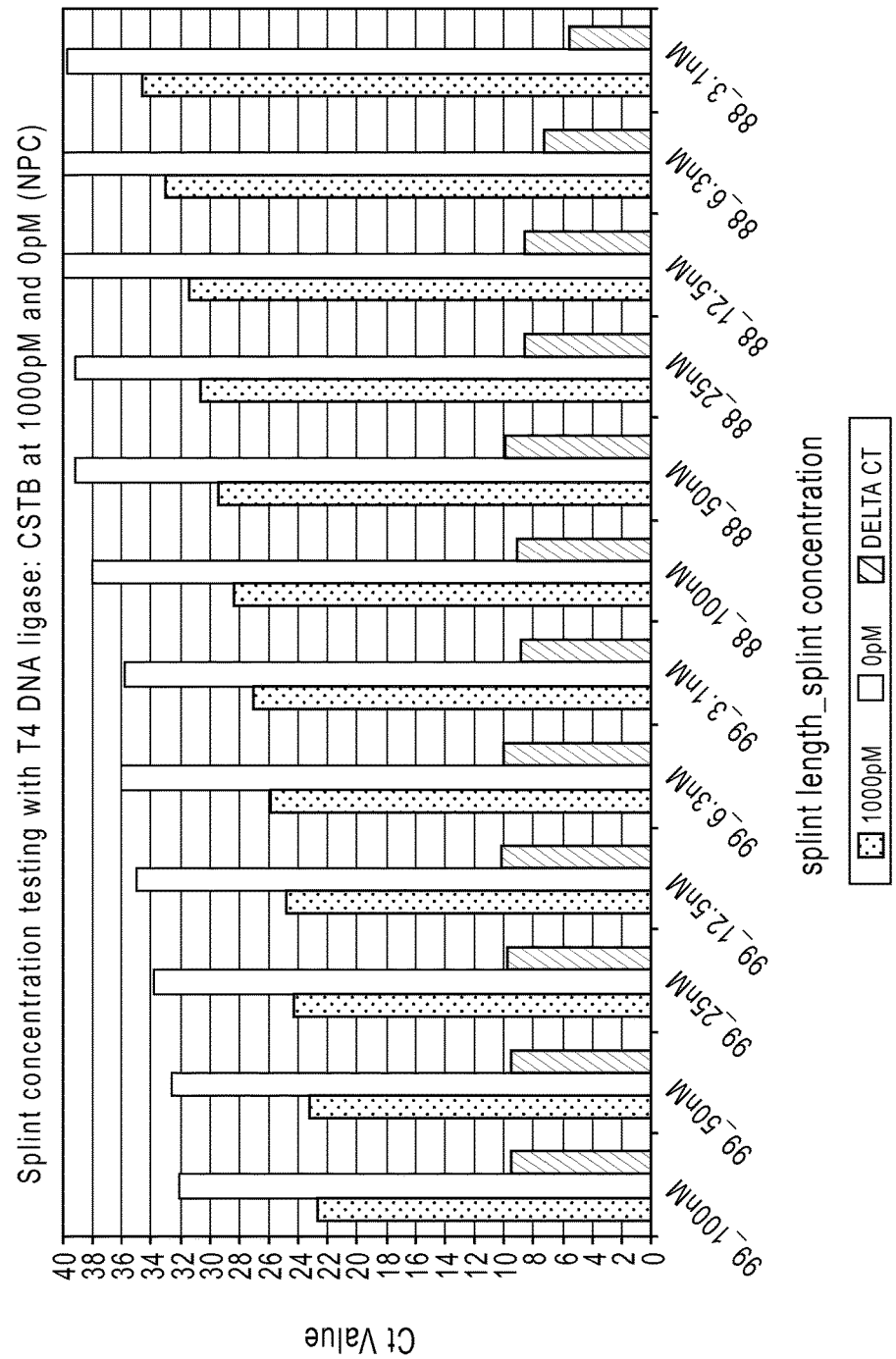

FIG. 7. Comparison of two different splint lengths at varying concentrations.

Figure 8:
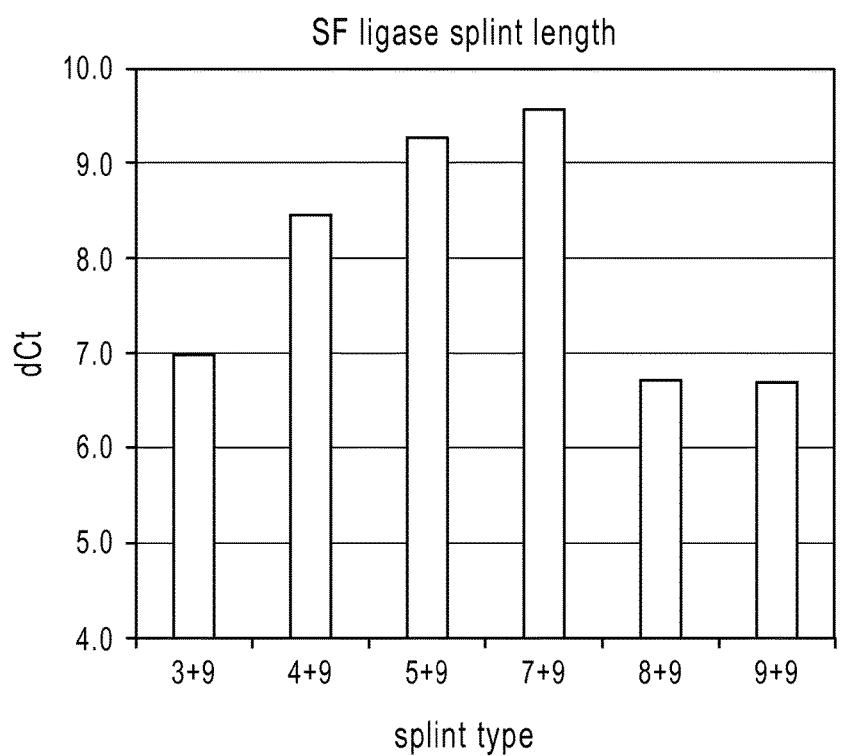

FIG. 8. Comparison of five different splint lengths.

Figure 9:
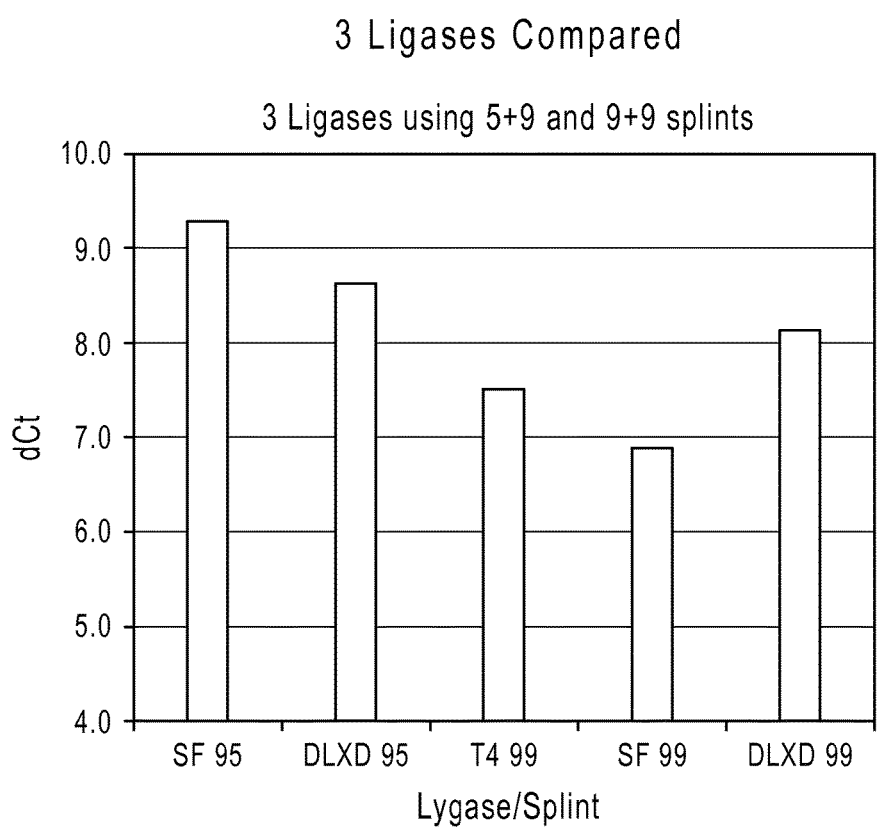

FIG. 9. Comparison of T4 ligase to two different SF ligases (e.g., SF and DLxD).

DETAILED DESCRIPTION

Disclosed herein are methods for performing proximity ligation assays. In typical or conventional proximity ligation assay (PLA) processes (FIG. 1), a probe mix and sample are combined into a binding reaction. Following the binding reaction, the ligation reaction mixture is added in order to carry out the ligation reaction. To prepare the ligation reaction mixture, a ligase and ligation buffer are diluted. Following the ligation reaction, the ligated product is stabilized by protease digestion; the protease is then inactivated (e.g, using heat). A portion of the ligated product is transferred to a real-time PCR reaction mixture, then placed on a PCR reaction vessel (e.g., plate) in a qPCR instrument. Detection and quantification of the ligated product then proceeds using standard techniques.

Figure 1:
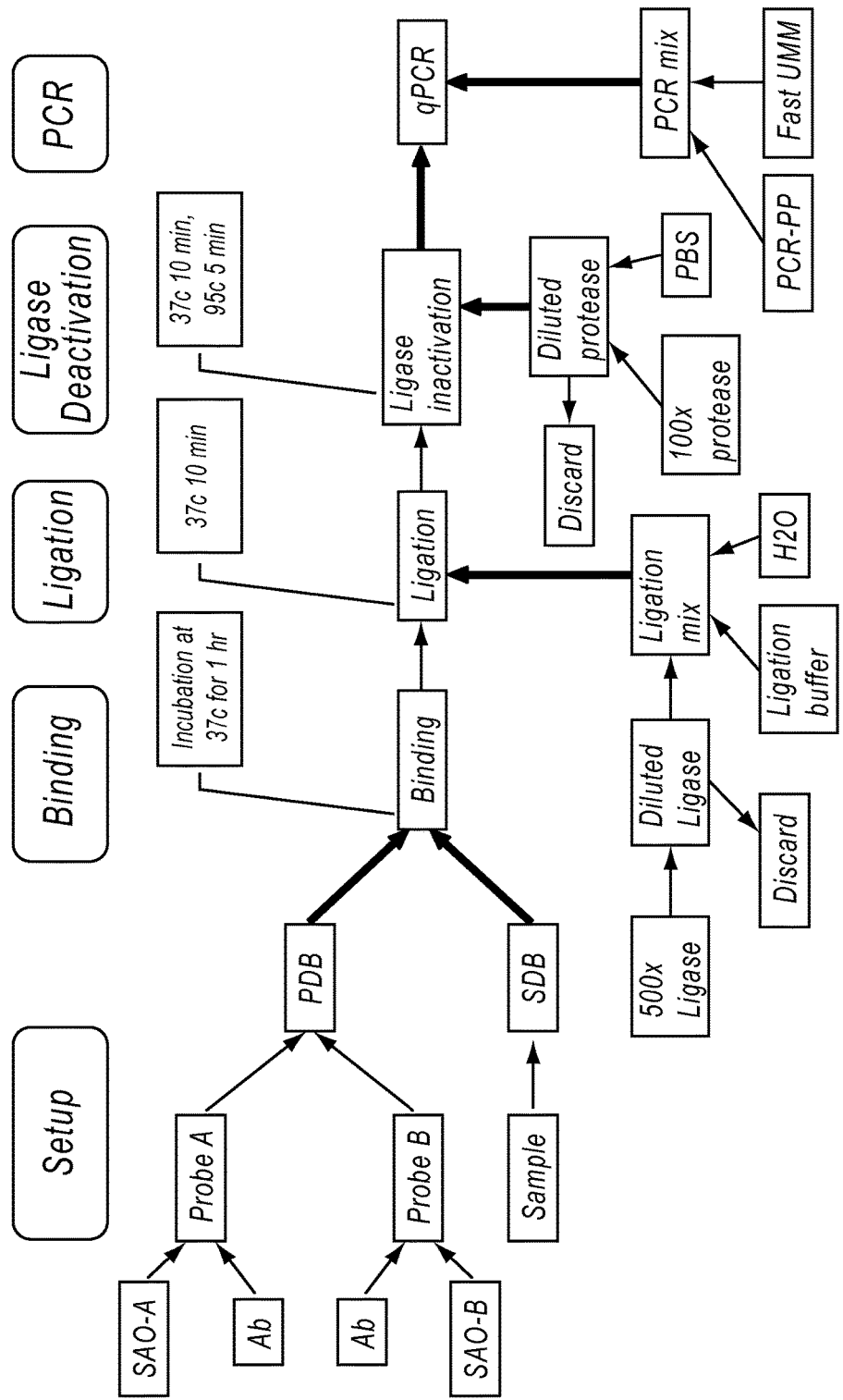
FIG. 1. A schematic diagram of an exemplary typical or conventional PLA process.
Figure 2:
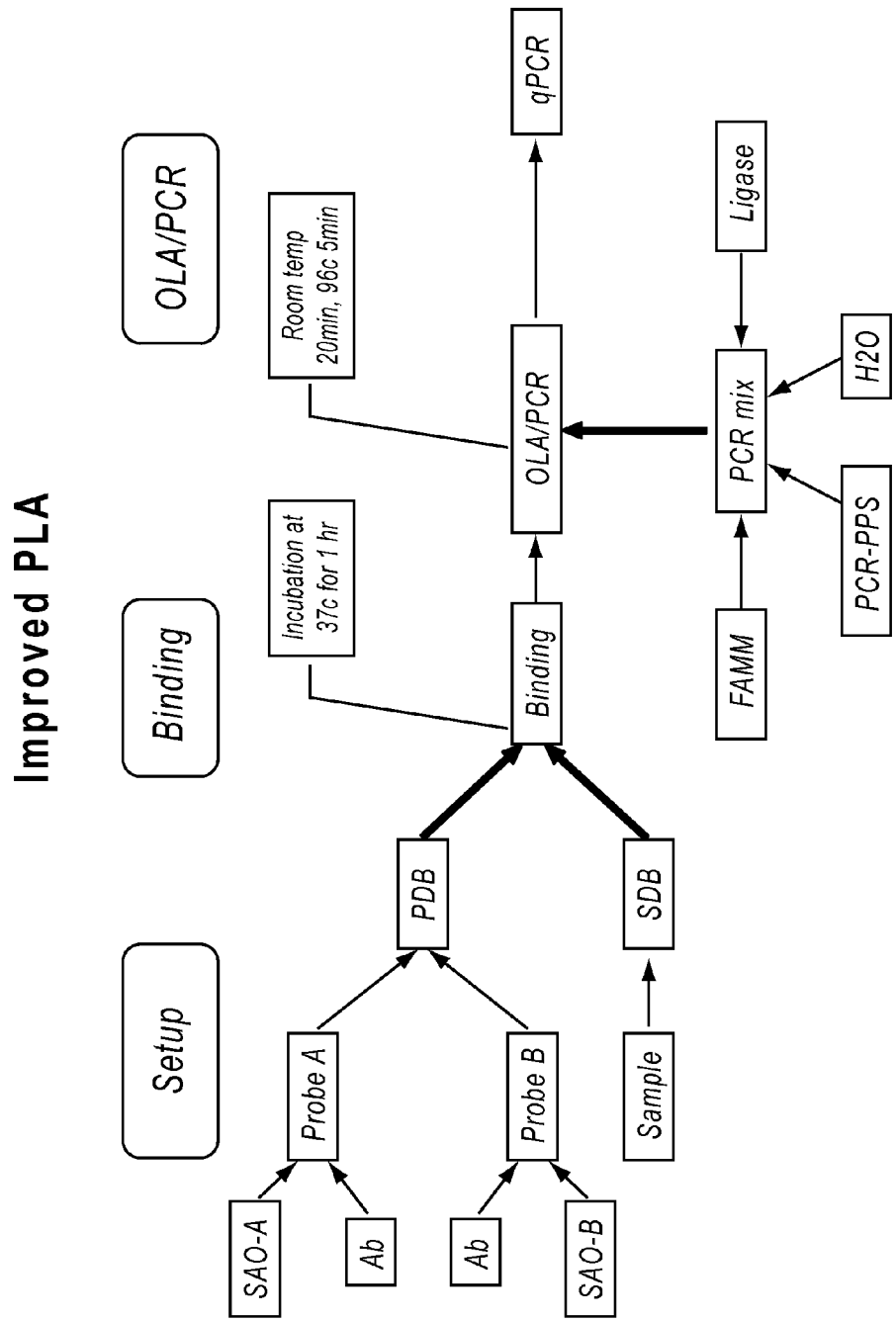
FIG. 2. A schematic diagram of an exemplary improved PLA process (as disclosed herein).

In one embodiment of the improved PLA process disclosed herein, a cell lysate may be prepared and a ligation buffer added thereto. To that mixture may then be added a proximity probe mixture, a ligase, and a PCR mixture (which may include, for example, a thermostable polymerase). This combined reaction mixture can then incubated for a suitable amount of time (e.g., one hour, 37° C.), the ligase optionally inactivated (e.g., using heat) and PCR performed directly on the mixture. A schematic of an exemplary embodiment of the improved PLA process is illustrated in FIG. 2. As shown therein, the binding reaction is the same as that shown in FIG. 1. However, in some embodiments of the improved PLA processes, the ligase is added to the real-time PCR mixture which is then added directly to the binding reaction. In some embodiments, this reaction mixture is then deposited onto a reaction plate and then analyzed by a qPCR instrument. Detection and quantification of the ligated product then proceeds using standard techniques.

In some embodiments, the lesser dilution factor provided thereby may result in a higher PLA probe concentration in the ligation reaction. The increased probe concentration may cause increased background signal, which may be minimized by using a short splint oligonucleotide at reduced concentration. For instance, a suitable splint oligonucleotide may be 14 nucleotides in length (e.g., at least five nucleotides in the 3' end and at least nine nucleotides in the 5' end; 5+9). To ensure the ligation efficiency, a small footprint ligase (SFL) may be used. In some embodiments, to further simplify the ligation-PCR step, the typical addition of ATP to the ligation reaction may be omitted. Instead, one may optionally use an ATP-enriched SFL (e.g., an SFL that is exposed to or contacted with an abundance or additional supply of ATP for some period of time). This enrichment step may be especially useful when co-substrates for other ligases are used. Thus, the binding reaction may be assembled by combining proximity probes and samples containing target molecule(s), and incubating the mixture such that binding between the probes and the target molecule(s) occurs. In some embodiments, after the binding reaction, a ligation-PCR mix (e.g., comprising a short splint oligo (e.g., an oligonucleotide that is at least 6 nucleotides, e.g., 6, 7, 8, 9, 10, 11, 12, 13, 14, 15, 16, 17, 18, 19, 20 or more nucleotides) in length, an SFL, and standard real-time PCR components) may be added. In some other embodiments, the ligation reaction may then take place at room-temperature, and the product amplified and quantitated by real-time PCR. In some embodiments, the ligase may be deactivated (e.g., using heat). The ligated product may then be subjected to real-time PCR immediately or following storage. Thus, the various embodiments of the novel work flows for improved PLA processes as disclosed herein provide reduced dilution factors which enable one to accomplish ligation and PCR in a single reaction mixture (e.g., or in a single step without intermediate/intervening steps). In some preferred embodiments, a short splint oligonucleotide and an SFL may also be used to control any increased background reactions. In additional embodiments, the SFL may be pre-enriched using ATP.

Figure 3A:
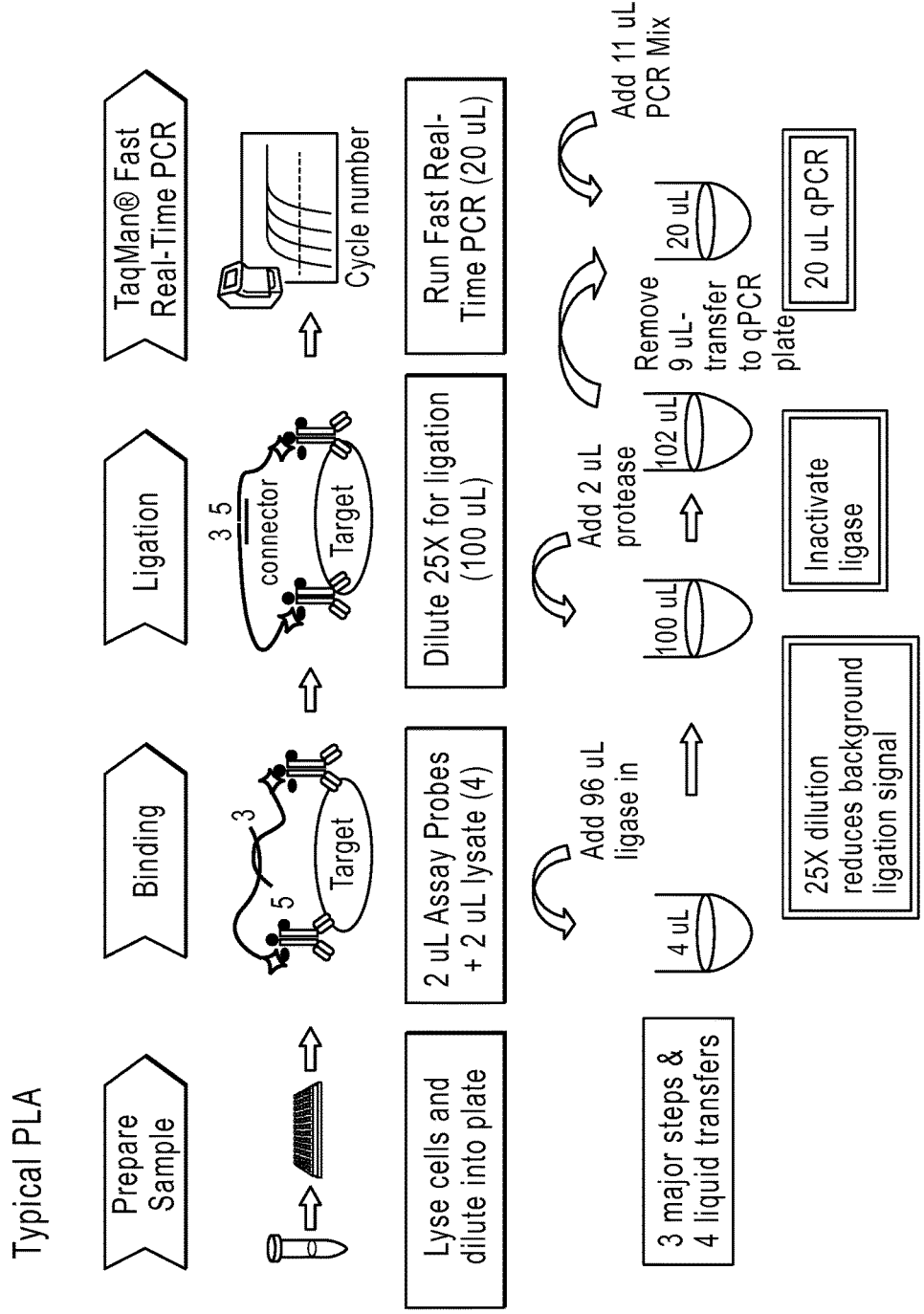
FIG. 3A—A schematic diagram of an exemplary typical or conventional PLA workflow.
Figure 3B:
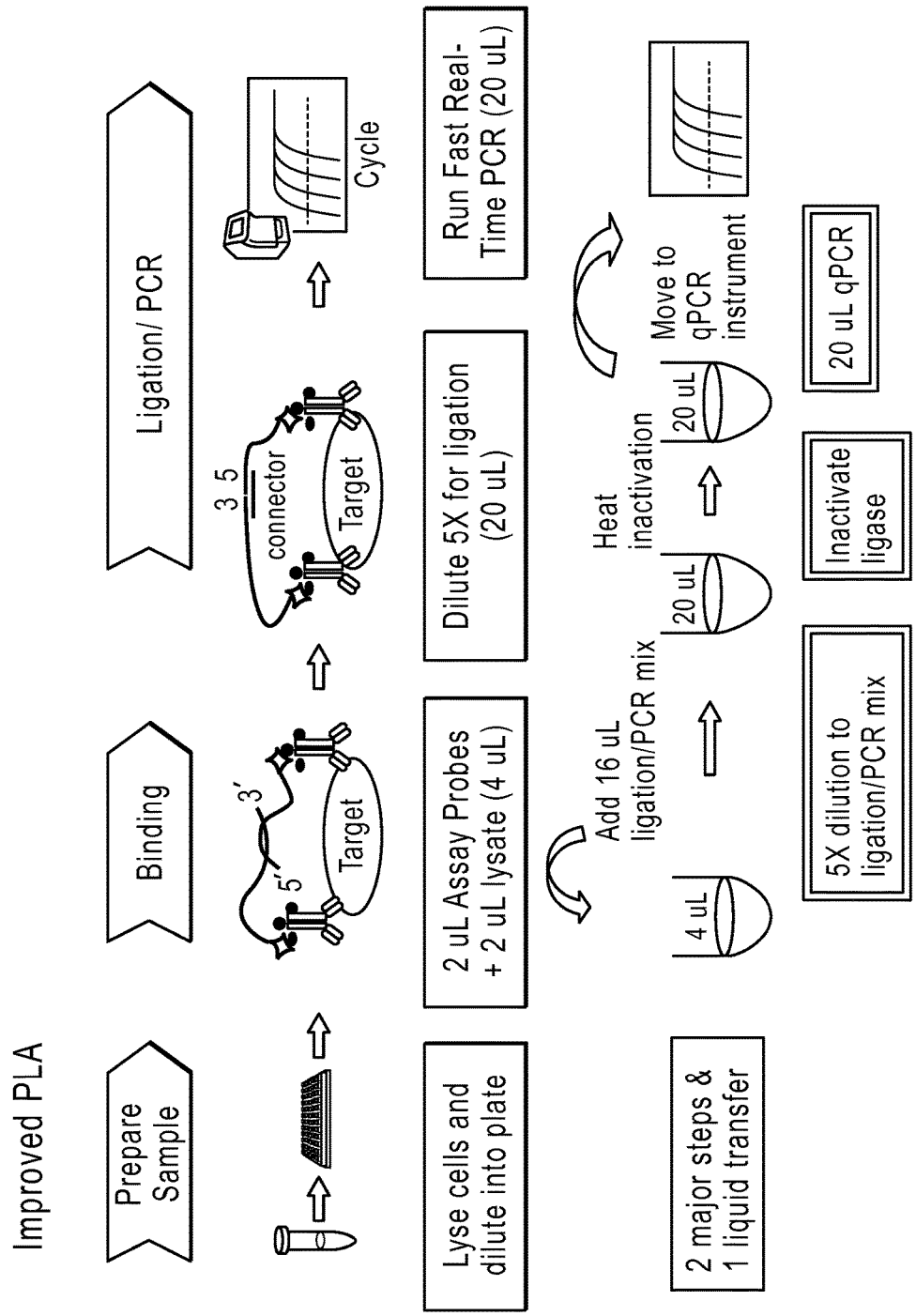

Exemplary typical and improved PLA processes are further compared in FIGS. 3A and 3B. As shown therein, the typical processes include sample preparation, a binding reaction, ligation, ligase inactivation using a protease, protease inactivation (e.g., using heat), followed by real-time PCR. To carry out the PCR step in typical PLA processes, a portion of the reaction mixture containing the inactivated ligase and protease is usually transferred to a PCR plate, and the "PCR mix" (e.g., containing primers, dNTPs, polymerase, and the like) added thereto. As shown in FIG. 3B, the disclosed improved processes can eliminate the use of a protease and dilution of the reaction mixture prior to PCR. As shown therein, the ligase may be inactivated using, for example, heat, and the resultant reaction mixture placed directly into a qPCR assay/instrument. Thus, simplified, improved PLA work flows can use entire binding reaction products in a real-time PCR assay (e.g., in a multi-plate well). This provides an improved work-flow and reduced dilution of the reaction mixture. As a result, in some embodiments of the improved PLA processes, the PCR reaction mixture contains a higher concentration of the ligated product (e.g., the target nucleic acid). In some embodiments, the improvement provided by the improved PLA processes can be measured as the dCT of the reaction (e.g., a 1, 2, 3, 4, 5, 6, 7, 8, 9, 10, or more signal (dCT); see, for example, FIG. 4A and FIG. 4B). Sensitivity of the improved PLA processes as compared to typical PLA processes can also be observed (e.g., as fold-change; see, for example, FIG. 5).

The processes described herein provide for, in some embodiments, detecting a protein in a test sample, the methods comprising contacting the protein with at least two probes having binding specificity therewith, each of the two probes comprising at least one oligonucleotide; ligating the oligonucleotides to produce a ligated oligonucleotide; amplifying the ligated oligonucleotide in a single reaction mixture; and, detecting amplification of the ligated oligonucleotide. In some embodiments, a third oligonucleotide may also be used to bridge each of the oligonucleotides attached to each of the probes. In some embodiments, one or more of the probes is an antibody. In certain embodiments, at least one of the oligonucleotides comprises at least three nucleotides. Some embodiments provide for use of a SFL, which may optionally be contacted with adenosine triphosphate (ATP) prior to use, for ligation of the oligonucleotides. Any type of amplification procedure may be used such as, without limitation, polymerase chain reaction (PCR) (e.g., quantitative PCR). In some embodiments, it may be beneficial to inactivate the ligase prior to amplification (e.g., using a protease, heat, or any other methods known in the art). Other embodiments of the inventions described herein will be apparent to the skilled artisan from the disclosure provided herein.

In some embodiments, a method for detecting a target in a sample is provided where the method includes the steps of binding a first and a second probe, each of which binds specifically to the target, wherein each of the probes comprises an oligonucleotide portion (or tail); ligating the first and second oligonucleotide tails thereby producing a ligated oligonucleotide template; and, performing a polymerase chain reaction (PCR) of the oligonucleotide template across the first and second oligonucleotide tails to quantify the said template. In some embodiments, the ligation and PCR steps may be performed in the same reaction mixture. In other embodiments, the method may include binding a first and a second probe, wherein each probe binds specifically to the target, each of the probes comprise a oligonucleotide tail; ligating the oligonucleotide tails to produce a ligated oligonucleotide template and amplifying the template by PCR in a single step to produce an amplified template; and, quantitating the amplified template. The probes may comprise antibodies which specifically bind to the target. The oligonucleotides may be ligated using a splint oligonucleotide (e.g., splint oligos of at least 6 nucleotides in length having 3' and 5' overhangs of, for example, 9+9, 9+8, 9+7, 9+6, 9+5, 8+8, 5+3, 4+7, 3+3 nucleotides, or any other possible variations in length or symmetry as contemplated and described in further detail below). In some embodiments, the ligase may be pre-enriched using ATP and/or inactivated using, for example, one or more proteases and/or heat. The amplified template may be quantified by any suitable method including, for example, real-time PCR (e.g., a TaqMan® assay or a molecular beacon assay).

The improved processes disclosed and/or exemplified herein provide reduced work times from process start time to collection of results (e.g., faster), reduced hands-on time (e.g., simpler and cheaper), reduced lab plasticware usage (e.g., cheaper and more environmentally sound ("greener")), and increased signals and sensitivities (e.g., more sensitive). In some embodiments, these improved processes provide simplified work flows by combining ligation and PCR steps, reduced dilution factors from the binding step to the ligation step, reduced binding probe concentrations to enable reduced dilution factors, use of shorter connector oligonucleotides (e.g., as few as 6 nucleotides in length) to control background signals, use of lower connector oligonucleotide concentrations to control background signals, use of SF ligases to enable use of shorter connector oligonucleotide lengths, ATP-enriched SF ligase purification schemes to omit ATP in ligation-PCR step, and/or enabling use of the entire reaction volume to improve PLA signal and sensitivity.

The methods described herein are particularly useful in that the same may be used with various systems for detecting proteins. Exemplary of such systems include, for example, TaqMan® Protein Assays. TaqMan® Protein Assays are an adapted form of PLA™, a proximity ligation assay technology that combines antibody-protein binding with detection of the reporter nucleic acid by real-time PCR. Applied Biosystems has optimized this technique for use with crude cell and tissue lysates and combined it with TaqMan® chemistry to create a highly sensitive and specific process for measuring protein expression in small samples. Assays have been developed for the detection of OCT3/4, NANOG, SOX2, and LIN28 in human embryonic stem cells, as well as ICAM1 and CSTB to measure relative quantification in human cells. The basic steps of such assays include binding of a protein target by paired assay probes, ligation of the oligonucleotides by a DNA ligase, and amplification of the ligation product by TaqMan® real-time PCR assay. The probes used in the first step are typically target-specific antibodies conjugated to oligonucleotides through a biotin-streptavidin (SA) linkage. Each oligonucleotide in the pair presents a 5' or 3' end that are brought into proximity when the assay probes bind to two different epitopes on the target protein. The substrate for the ligase is typically a bridge structure formed by hybridization of a third oligonucleotide to the oligonucleotide ends of the assay probe pair. This structure forms preferentially when the assay probes are in proximity to each other. The ligation product typically serves the template in the TaqMan® real-time PCR assay. The systems may be used to, for example, to perform protein analysis on small samples (e.g., stem cells, germ cell tumors), correlate and/or validate results from RNA and protein quantitation, analyze post-translational modifications, validate siRNA-induced gene silencing, and/or validate gene transfection/transduction experiments. Data generated using these systems may be anlayzed using software such as, for instance, ProteinAssist™ software package (Applied Biosystems™).

To more clearly and concisely describe and point out the subject matter of the present disclosure, the following definitions are provided for specific terms, which are used in the following description and the appended claims. Throughout the specification, exemplification of specific terms should be considered as non-limiting examples.

As used herein the terms "nucleotide" or "nucleotide base" refer to a nucleoside phosphate. It includes, but is not limited to, a natural nucleotide, a synthetic nucleotide, a modified nucleotide, or a surrogate replacement moiety or universal nucleotide (e.g., inosine). The nucleoside phosphate may be a nucleoside monophosphate, a nucleoside diphosphate or a nucleoside triphosphate. A "nucleotide" refers to a nucleotide, nucleoside or analog thereof. Optionally, the nucleotide is an N- or C-glycoside of a purine or pyrimidine base. (e.g., deoxyribonucleoside containing 2-deoxy-D-ribose or ribonucleoside containing D-ribose). Examples of other analogs include, without limitation, phosphorothioates, phosphoramidates, methyl phosphonates, chiral-methyl phosphonates, 2-O-methyl ribonucleotides. Nucleotide bases usually have a substituted or unsubstituted parent aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, purines such as 2-aminopurine, 2,6-diaminopurine, adenine (A), ethenoadenine, N6-Δ2-isopentenyladenine (6iA), N6-Δ2-isopentenyl-2-methylthioadenine (2ms6iA), N6-methyladenine, guanine (G), isoguanine, N2-dimethylguanine (dmG), 7-methylguanine (7 mG), 2-thiopyrimidine, 6-thioguanine (6sG) hypoxanthine and 06-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, 04-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); etc. In certain embodiments, nucleotide bases are universal nucleotide bases. Additional exemplary nucleotide bases can be found, e.g., in Fasman, 1989, Practical Handbook of Biochemistry and Molecular Biology, pp. 385-394, CRC Press, Boca Raton, Fla., and the references cited therein. A "universal base", as used herein, is a base that is complementary to more than one other base. Fully universal bases can pair with any of the bases typically found in naturally occurring nucleic acids. The base need not be equally capable of pairing with each of the naturally occurring bases. Alternatively, the universal base may pair only or selectively with two or more bases but not all bases. Optionally the universal base pairs only or selectively with purines, or alternatively with pyrimidines. If so desired, two or more universal bases can be included at a particular position in a probe. A number of universal bases are known in the art including, but not limited to, hypoxanthine, 3-nitropyrrole, 4-nitroindole, 5-nitroindole, 4-nitrobenzimidazole, 5-nitroindazole, 8-aza-7-deazaadenine, 6H,8H-3,4-dihydropyrimido[4,5-c][1,2]oxazin-7-one (P. Kong Thoo Lin.

and D. M. Brown, Nucleic Acids Res., 1989, 17, 10373-10383), 2-amino-6-methoxyaminopurine (D. M. Brown and P. Kong Thoo Lin, Carbohydrate Research, 1991, 216, 129-139), etc. Hypoxanthine is one preferred fully universal base. Nucleosides comprising hypoxanthine include, but are not limited to, inosine, isoinosine, 2'-deoxyinosine, and 7-deaza-2'-deoxyinosine, 2-aza-2'deoxyinosine. Naturally occurring and synthetic analogs may also be used, including for example hypoxanthine, 2-aminoadenine, 2-thiouracil, 2-thiothymine, 5-$N^4$ ethencytosine, 4-aminopyrrazolo[3,4-d]pyrimidine and 6-amino-4-hydroxy[3,4-d]pyrimidine, among others. The nucleotide units of the oligonucleotides may also have a cross-linking function (e.g. an alkylating agent).

A nucleoside is usually a compound having a nucleotide base covalently linked to the C-1' carbon of a pentose sugar. In certain embodiments, the linkage is via a heteroaromatic ring nitrogen. Typical pentose sugars include, but are not limited to, those pentoses in which one or more of the carbon atoms are each independently substituted with one or more of the same or different —R, —OR, —NRR or halogen groups, where each R is independently hydrogen, ($C_1$-$C_6$) alkyl or ($C_5$-$C_{14}$) aryl. The pentose sugar may be saturated or unsaturated. Exemplary pentose sugars and analogs thereof include, but are not limited to, ribose, 2'-deoxyribose, 2'-($C_1$-$C_6$)alkoxyribose, 2'-($C_5$-$C_{14}$)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-($C_1$-$C_6$)alkylribose, 2'-deoxy-3'-($C_1$-$C_6$)alkoxyribose and 2'-deoxy-3'-($C_5$-$C_{14}$) aryloxyribose. One or more of the pentose carbons of a nucleoside may be substituted with a phosphate ester, as disclosed in, for example, U.S. Pat. No. 7,255,994. In certain embodiments, the nucleosides are those in which the nucleotide base is a purine, a 7-deazapurine, a pyrimidine, a universal nucleotide base, a specific nucleotide base, or an analog thereof. Nucleotide analogs include derivatives in which the pentose sugar and/or the nucleotide base and/or one or more of the phosphate esters of a nucleoside may be replaced with its respective analog. Exemplary pentose sugar analogs and nucleotide base analog are described above. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions. Other nucleotide analogs are nucleotide analog monomers which can be polymerized into polynucleotide analogs in which the DNA/RNA phosphate ester and/or sugar phosphate ester backbone is replaced with a different type of linkage. Exemplary polynucleotide analogs include, but are not limited to, peptide nucleic acids, in which the sugar phosphate backbone of the polynucleotide is replaced by a peptide backbone. The internucleoside linkages can be a phosphodiester linkage, although other linkages (e.g., scissile linkages which can be substantially cleaved under conditions in which phosphodiester linkages are not substantially cleaved) can be used. For example, a linkage that contains an AP endonuclease sensitive site, for example an abasic residue, a residue containing a damaged base that is a substrate for removal by a DNA glycosylase, or another residue or linkage that is a substrate for cleavage by an AP endonuclease, or a disaccharide nucleoside.

As used herein, the term "oligonucleotide" ("oligo") or "polynucleotide" may refer to an oligomer of nucleotides or derivatives thereof. Polynucleotides include double- and single-stranded DNA, as well as double- and single-stranded RNA, DNA:RNA hybrids, peptide-nucleic acids (PNAs) and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbonates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The oligomers may also include modified bases, and/or backbones (e.g., modified phosphate linkage or modified sugar moiety). Non-limiting examples of synthetic backbones that confer stability and/or other advantages to the oligomers may include phosphorothioate linkages, peptide nucleic acid, locked nucleic acid (Singh, et al. Chem Commum 4:455-456 (1998)), xylose nucleic acid, and/or analogues thereof. In other cases, the polynucleotide can contain non-nucleotidic backbones, for example, polyamide (e.g., peptide nucleic acids (PNAs)) and polymorpholino (commercially available from the Anti-Virals, Inc., Corvallis, Oreg., as Neugene™ polymers), and other synthetic sequence-specific nucleic acid polymers providing that the polymers contain nucleobases in a configuration which allows for base pairing and base stacking, such as is found in DNA and RNA.

Oligonucleotides and/or polynucleotides may be any length "n." For example, n may be any of 1, 2, 4, 6, 8, 12, 16, 20, 22, 24, 26, 28, 30, 32, 34, 36, 38, 40 etc. number of nucleotides. The polynucleotide structure $(N)_n$ represents an oligonucleotide consisting of n number of nucleotides N (e.g., $(I)_8$ is representative of an oligonucleotide having the sequence 11111111; or $(A)_{12}$ is representative of an oligonucleotide having the sequence AAAAAAAAAAAA). Other types of oligonucleotides or polynucleotides may also be suitable for use as would be understood to one of skill in the art from this disclosure.

Oligonucleotides and/or polynucleotides may optionally be attached to one or more non-nucleotide moieties such as labels and other small molecules, large molecules such proteins, lipids, sugars, and solid or semi-solid supports, for example through either the 5' or 3' end. Labels include any moiety that is detectable using a detection method of choice, and thus renders the attached nucleotide or polynucleotide similarly detectable using a detection method of choice (e.g., using a SGC and/or detectable label). Optionally, the label emits electromagnetic radiation that is optically detectable or visible. In some cases, the nucleotide or polynucleotide is not attached to a label, and the presence of the nucleotide or polynucleotide is directly detected.

As used herein, the term "nucleic acid" refers to polymers of nucleotides or derivatives thereof. As used herein, the term "target nucleic acid" refers to a nucleic acid that is desired to be amplified in a nucleic acid amplification reaction. For example, the target nucleic acid comprises a nucleic acid template. In some embodiments, the target nucleic acid may be the product of the ligation of at least two oligonucleotides to one another.

As used herein, the term "sequence" refers to a nucleotide sequence of an oligonucleotide or a nucleic acid. Throughout the specification, whenever an oligonucleotide/nucleic acid is represented by a sequence of letters, the nucleotides are in 5' to 3' order from left to right. For example, if the polynucleotide contains bases Adenine, Guanine, Cytosine, Thymine, or Uracil, the polynucleotide sequence can be represented by a corresponding succession of letters A, G, C, T, or U), e.g., a DNA or RNA molecule. And, an oligonucleotide represented by a sequence $(I)_n(A)_n$ wherein n=1, 2, 3, 4 and so on, represents an oligonucleotide where the 5' terminal nucleotide(s) is inosine and the 3' terminal nucleotide(s) is adenosine.

Oligonucleotides and/or polynucleotides can optionally be regarded as having "complementary" sequences if the same may hybridize to one another. The term "hybridization" typically refers to the process by which oligonucleotides and/or polynucleotides become hybridized to each other. The adjectival term "hybridized" refers to two polynucleotides which are bonded to each other by two or more sequentially adjacent base pairings. Typically, these terms refer to "specific hybridization". Two oligonucleotides and/or polynucleotides may selectively (or specifically) hybridize to each other if they bind significantly or detectably to each other under stringent hybridization conditions when present in a complex polynucleotide mixture such as total cellular or library DNA. In some embodiments, for selective or specific hybridization, a positive signal is at least two times background, preferably 10 times background hybridization. Optionally, stringent conditions are selected to be about 5-10° C. lower than the thermal melting point for the specific sequence at a defined ionic strength pH. Stringent conditions are optionally in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Nucleic acids that do not hybridize to each other under stringent conditions are still substantially identical if the polypeptides which they encode are substantially identical. "Nonspecific hybridization" is used to refer to any unintended or insignificant hybridization, for example hybridization to an unintended polynucleotide sequence other than the intended target polynucleotide sequence. The uninentended polynucleotide sequence can be on the same or different polynucleotide from the intended target. In some cases, the only intended hybridization can be from Watson-Crick base pairing between two polynucleotides. Other kinds of intended base pairings can include base pairing between corresponding analogs of such nucleotides or between iso-cytidine and iso-guanine. In some cases where hybridization is only intended between complementary bases, any bonding between non-complementary bases is considered to be non-specific hybridization.

In some embodiments, complementary sequences may be those that, when hybridized together, may be efficiently ligated to a third polynucleotide that has hybridized adjacently to it. Similarly, nucleotide residues can be regarded as complementary if when both are base-paired with each other within two hybridized polynucleotides, either nucleotide can be ligated in a template-driven ligation reaction when situated as the terminal nucleotide in its polynucleotide. Nucleotides that are efficiently incorporated by DNA polymerases opposite each other during DNA replication under physiological conditions are also considered complementary. In an embodiment, complementary nucleotides can form base pairs with each other, such as the A-T/U and G-C base pairs formed through specific Watson-Crick type hydrogen bonding between the nucleobases of nucleotides and/or polynucleotides positions antiparallel to each other. The complementarity of other artificial base pairs can be based on other types of hydrogen bonding and/or hydrophobicity of bases and/or shape complementarity between bases. In appropriate instances, polynucleotides can be regarded as complementary when the same may undergo cumulative base pairing at two or more individual corresponding positions in antiparallel orientation, as in a hybridized duplex. Optionally there can be "complete" or "total" complementarity between a first and second polynucleotide sequence where each nucleotide in the first polynucleotide sequence can undergo a stabilizing base pairing interaction with a nucleotide in the corresponding antiparallel position on the second polynucleotide. "Partial" complementarity describes polynucleotide sequences in which at least 20%, but less than 100%, of the residues of one polynucleotide are complementary to residues in the other polynucleotide. A "mismatch" is present at any position in the two opposed nucleotides that are not complementary. In some ligation assays, a polynucleotide can undergo substantial template-dependent ligation even when it has one or more mismatches to its hybridized template. Optionally, the polynucleotide has no more than 4, 3, or 2 mismatches, e.g., 0 or 1 mismatch, with its template. In some assays, the polynucleotide will not undergo substantial template-dependent ligation unless it is at least 60% complementary, e.g., at least about 70%, 80%, 85%, 90%, 95% or 100% complementary to its template.

"Degenerate", with respect to a position in a polynucleotide that is one of a population of polynucleotides, means that the identity of the base of the nucleoside occupying that position varies among different members of the population. A population of polynucleotides in this context is optionally a mixture of polynucleotides within a single continuous phase (e.g., a fluid). The "position" can be designated by a numerical value assigned to one or more nucleotides in a polynucleotide, generally with respect to the 5' or 3' end. For example, the terminal nucleotide at the 3' end of an extension probe may be assigned position 1. Thus in a pool of extension probes of structure 3'-XXXNXXXX-5', the N is at position 4. A position is said to be k-fold degenerate if it can be occupied by nucleosides having any of k different identities. For example, a position that can be occupied by nucleosides comprising either of 2 different bases is 2-fold degenerate.

A "solid support", as used herein, typically refers to a structure or matrix on or in which ligation and/or amplification reagents (e.g., nucleic acid molecules, microparticles, and/or the like) may be immobilized so that they are significantly or entirely prevented from diffusing freely or moving with respect to one another. The reagents can for example be placed in contact with the support, and optionally covalently or noncovalently attached or partially/completely embedded. The terms "microparticle," "beads", "microbeads", etc., refer to particles (optionally but not necessarily spherical in shape) having a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). Microparticles (e.g., Dynabeads from from Dynal, Oslo, Norway) may be made of a variety of inorganic or organic materials including, but not limited to, glass (e.g., controlled pore glass), silica, zirconia, cross-linked polystyrene, polyacrylate, polymehtymethacrylate, titanium dioxide, latex, polystyrene, etc. Magnetization can fecilitate collection and concentration of the microparticle-attached reagents (e.g., polynucleotides or ligases) after amplification, and facilitates additional steps (e.g., washes, reagent removal, etc.). In certain embodiments of the invention a population of microparticles having different shapes sizes and/or colors can be used. The microparticles can optionally be encoded, e.g., with quantum dots such that each microparticle can be individually or uniquely identified.

As used herein the term "reaction mixture" refers to the combination of reagents or reagent solutions, which are used to carry out a chemical analysis or a biological assay. In some embodiments, the reaction mixture comprises all necessary components to carry out a nucleic acid (DNA) synthesis/amplification reaction. As described above, such reaction mixtures may include at least one amplification primer pair suitable for amplifying a nucleic acid sequence of interest (e.g., target nucleic acid). As described above, a suitable reaction mixture may also include a "master mix" containing the components (e.g., typically not including the primer pair) needed to perform an amplification reaction (e.g., detergent, magnesium, buffer components, etc.). Other embodiments of reaction mixtures are also contemplated herein as would be understood by one of skill in the art.

As used herein, the terms "reagent solution" or "solution suitable for performing a DNA synthesis reaction" refer to any or all solutions, which are typically used to perform an amplification reaction or DNA synthesis. They include, but are not limited to, solutions used in DNA amplification methods, solutions used in PCR amplification reactions, or the like. The solution suitable for DNA synthesis reaction may comprise buffer, salts, and/or nucleotides. It may further comprise primers and/or DNA templates to be amplified. One or more reagent solutions are typically included in the reactions mixtures or master mixes described herein.

As used herein, the term "primer" or "primer sequence" refers to a short linear oligonucleotide that hybridizes to a target nucleic acid sequence (e.g., a DNA template to be amplified) to prime a nucleic acid synthesis reaction. The primer may be a RNA oligonucleotide, a DNA oligonucleotide, or a chimeric sequence (e.g., comprising RNA and DNA). The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about any of, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, (and so on) nucleotides in length.

In some embodiments, the terms "probe(s)", "oligonucleotide(s)" and/or "primer(s)" may be interchangeable terms herein, so that any one of these may be taken as a reference to another. The terms "polynucleotide", "oligonucleotide", "probe", "primer", "template", "nucleic acid" and the like may be taken to refer to a populations or pools of individual molecules that are substantially identical across their entire length or across a relevant portion of interest. For example, the term "template" may indicate a plurality of template molecules that are substantially identical, etc. In the case of polynucleotides that are degenerate at one or more positions, it will be appreciated that the degenerate polynucleotide may comprise a plurality of polynucleotide molecules, which have sequences that are substantially identical only at the nondegenerate position(s) and differ in sequence at the degenerate positions. Thus, reference to "a" polynucleotide (e.g., "a" primer, probe, oligonucleotide, template, etc.) may be taken to mean a population of substantially identical polynucleotide molecules, such that the plural nature of a population of substantially identical nucleic acid molecules need not be explicitly indicated, but may if so desired. These terms are also intended to provide adequate support for a claim that explicitly specifies a single polynucleotide molecule itself.

"Ligation" involves the formation of a covalent bond or linkage between the termini of two or more nucleic acids, e.g. oligonucleotides and/or polynucleotides, optionally in a template-driven reaction. Exemplary ligations may be carried out enzymatically to form a phosphodiester linkage between a 5' carbon of a terminal nucleotide of one oligonucleotide with 3' carbon of another oligonucleotide (e.g., using a ligase). The nature of the bond or linkage may vary widely and the ligation is preferably achieved enzymatically. The efficiency of ligation refers to the rate of ligation. Where the relative efficiency of ligation is specified in comparative or relative terms by comparison to a reference ligation assay, it is implicit that all other reagents and conditions (e.g., temperature, concentration of all reagents, pH, concentration of requisite ions such as Mg++ and Mn++, concentration of requisite cofactors such as NAD and/or ATP, salts, buffers, molar concentrations of all reagents, including enzyme, template, probe primer, oligonucleotides, etc) are otherwise kept identical. For example, a proviso that a ligase (e.g., an SFL (see below)) can ligate a short (e.g., less than 6 nucleotides) probe at least X % (e.g., where X is 100 or less; 100, 99, 95, 90, 85, 80, 75, 70, 50, 25, 10, 1, 0.5, 0.1, etc., or any increment in between) as efficiently as the ligase can ligate a corresponding octanucleotide, may be understood to mean that the rate of ligation of the shorter probe occurs at a rate that is at least X % of the rate of ligation of the octanucleotide, where all reagents except for the probes (e.g., primer, template, enzymes and any other reagents) and all reaction conditions (e.g., temperature, reagent concentrations, concentrations of any other reagents, etc) are kept invariant for practical purposes. It is understood that ligation efficiency in absolute or relative terms may increase or decrease depending on the exact reaction conditions used.

Optionally, ligation is performed under in-vitro conditions that have been experimentally determined to be suitable or optimal for ligase activity. Preferably, reaction conditions are kept substantially similar to in-vivo or physiological conditions in which a naturally-occurring form of the ligase being used is naturally active. Most preferably, the reaction conditions for a particular ligase are matched as closely as possible to exemplary in vitro ligation conditions described herein for that ligase. In other embodiments, the conditions are such that the reference ligation assay produces significant or detectable ligation within 30 minutes, within 10 minutes, within 1 minute, or within ten seconds. Another non-limiting example of a significant or detectable rate of ligation generates in the range of 100 pM of ligation product, optionally about 1000 pM or 10,000 pM, in an appropriate amount of time (e.g., 10 minutes).

Along similar lines, it should be understood that a statement that a result has occurred (e.g., ligation, binding) is intended to indicate that the result has occurred at a significant or substantial level or an enhanced level compared to when it has not occurred. For example, ligation is said to have not occurred if it is not significant, insubstantial or greatly reduced (e.g., reduced by at least 80%, 90%, 95% or 99% compared to when ligation does occur (e.g., under the conditions described in the last paragraph). In reference to ligation of two polynucleotides, the "proximal" terminus of either polynucleotide is the terminus that is intended to be ligated to the other polynucleotide. It is generally the terminus that is closer to the other polynucleotide, or the terminus that is contacted by the active site of the ligase, or the terminus that is eventually ligated to the other polynucleotide, while the opposite terminus is the "distal" terminus. The terminal nucleotide residue at the proximal terminus can be termed the proximal nucleotide, and the proximal nucleotide position optionally designated as position 1, the penultimate nucleotide position as position 2, etc. In some non-limiting instances of template-dependent ligation, the proximal termini of both polynucleotides are hybridized adjacently to each other.

An exemplary type of enzymatic ligation (double-stranded ligation) includes the formation of a covalent bond between nucleotides of a polynucleotide (e.g., resulting in circularization) or between two or more polynucleotides (e.g., a first double-stranded terminus of a first polynucleotide and a second different double-stranded terminus of a second polynucleotide). The polynucleotides may be different, or may be the same. Polynucleotides may also be ligated using a "splint" oligonucleotide which may be used to link nucleotides that the user desires to ligate (e.g., on the same or different polynucleotides). Optionally, the ends of both double-stranded termini may be joined irrespective of their sequences (e.g., blunt-end ligation, or non-homologous end joining).

In another variation, two double-stranded polynucleotides with protruding single-stranded ends that are complementary to each other can be ligated (e.g., cohesive-end ligation). In other instances, the ligation can ligate two single-stranded polynucleotides, either or both of which has optionally hybridized (annealed) to another nucleotide sequence. In template-dependent ligation, ligation between a first polynucleotide and a second polynucleotide occurs upon hybridization of at least a portion of either or both polynucleotides to a target sequence. The target sequence can be a portion of either polynucleotide (e.g., self-hybridization or hybridization to each other) or to a sequence on a third different polynucleotide (e.g., a "splint" oligonucleotide). The hybridized portion of the polynucleotide may be, for example, not more than 1, 2, 3, 4, 5, 6, 7, 8, 10, 15 or 20 nucleotides long. The hybridized portion is optionally a terminal portion of the nucleotide (e.g., includes the 5' or 3' nucleotide). For example, the hybridized portion can consist of the 5' or 3' terminal nucleotide, or the terminal 2, 3, 4, 5, 6, 7, 8, 10, 15 or 20 nucleotides of the 5' or 3' end. Optionally, ligation occurs when no mismatch is present within the hybridized portions.

In other cases, ligation occurs when one, two or three mismatches can be present within the hybridized portion. In some cases ligation does not occur when the terminal nucleotide and/or second-most terminal nucleotide and/or third-most terminal nucleotide is mismatched. As mentioned, the terminal nucleotides can be the 5'- or 3'-terminal nucleotides of the polynucleotide. An exemplary type of assay makes use of template-dependent ligation between a first single-stranded polynucleotide and a second single-stranded polynucleotide, where ligation can be effected when either or both polynucleotides is/are hybridized to a third different single-stranded polynucleotide. In some instances, both probes must hybridize to the template for significant ligation to occur. For ease of reference, the first polynucleotide is called the "initializing probe," the second polynucleotide called the "extension probe" and the third polynucleotide called the "template."

In some variations, (e.g., "nick ligation"), both probes must hybridize adjacently to each other on the template for ligation to occur. In some assays, the probes are adjacently hybridized and can be ligated only when a terminal nucleotide of the initializing probe is hybridized to a first nucleotide of the template and a terminal nucleotide of the extension probe is hybridized to a second nucleotide of the template, where the first and second nucleotides on the template are not separated by an intervening nucleotide of the template. In other embodiments, a few intervening nucleotides may be present between the first and second nucleotides on the template (e.g., 1, 2, 3 or more nucleotides). In such embodiments, a "gap-filling" step can be performed to extend the 3' terminus of one probe before it can be ligated to the 5' terminus of the other probe.

In the methods described herein, the terminal nucleotide of the initializing probe can be the 5' terminal nucleotide and the terminal nucleotide of the extension probe can be the 3' terminal nucleotide. Alternatively, the terminal nucleotide of the initializing probe can be the 3' terminal nucleotide and the terminal nucleotide of the extension probe can be the 5' terminal nucleotide. The ligation product of any one reaction can optionally be subjected to further ligation and/or non-ligation reactions in turn. For example, the ligation product can be used as the initializing probe or extension probe or template in a subsequent ligation. Also for example, it can be used as a template or primer for polymerase extension, such as in polymerase chain reaction (PCR). It can be cleaved enzymatically or chemically (for example when it has scissile linkages), treated with exo- or endonucleases, kinases, phosphatases, etc. The ends of a double-stranded product can be blunt-ended or filled in, capped, or adenylated, etc.

As used herein, "splint oligonucleotide," "splint oligo," or "connector" refers to an oligonucleotide that is used to provide an annealing site or a "ligation template" for joining two ends of a nucleic acid molecule or molecules using a ligase or another enzyme with ligase activity. The ligation splint holds the ends adjacent to each other and "creates a ligation junction" between the 5'-phosphorylated and a 3'-hydroxylated ends that are to be ligated. For example, when a ligation splint oligo is used to join the 3'-end of a first probe oligo (oligo A) to the 5'-end of a second probe oligo, the ligation splint oligo has a sequence complementary to the 3'-end of oligo A (e.g., oligo tail sequence, and a second neighboring sequence (e.g., an adjacent sequence) that is complementary to the 5'-end of oligo B (FIG. 4A and FIG. 4B).

In some embodiments of the improved PLA processes splint oligos can be either symmetrical or asymmetrical depending on the number of nucleotides that hybridize to each of the two oligo probes it is connecting or ligating. FIG. 4A and FIG. 4B diagrams asymmetrical and symmetrial splint types for use in the improved PLA processes as described herein. In some embodiments, asymmetrical splints (or "connectors") span across the two separate oligo probes (e.g., probe oligo A and B) with one of the ends of the splint (e.g., either the 3'-end or the 5'-end) having more nucleotides that hybridize to one of the probe oligos than the other end of the splint has nucleotides that hybridize to the alternative probe oligo (FIG. 4A). In other embodiments, symmetrical splints span across the two separate oligo probes (e.g., probe oligo A and B) with both ends of the splint (e.g., the 3' end and the 5' end) having equal number of nucleotides that hybridize to each of the two probe oligos (FIG. 4B).

Both asymmetrical and symmetrical splints can have any number of intervening nucleotides between each of its 3' and 5' ends that hybridize to the separate probe oligos. Alternatively, there may be no intervening nucleotides between each of the 3' and 5' ends that hybridize to the probe oligos. In preferred embodiments, splint oligonucleotides (oligos) are at least 6 nucleotides long (e.g., 6, 7, 8, 9, 10, 11, 12, 13, 14, 15, 16, 17, 18, 19, 20 or more). In certain other embodiments, each of the 3'- or 5'-ends of the splint oligo will comprise at least 3 (e.g., 3, 4, 5, 6, 7, 8, 9, 10 or more) nucleotides that separately hybridize to (or "overlap") an oligo probe, herein referred to as the "overhang" region.

In some embodiments of the improved PLA processes the splint oligo is blocked at its 3'-end. The blocking agent can be any covalently connected moiety that prevents polymerase activity. This 3' blocked splint oligo is then prevented from interfering with the PCR reaction part of the improved PLA process. In some embodiments, for example, the 3' blocking agent can include, but is not limited to, 3'-fluoro-, 3'-bromo-, 3'-iodo-, 3'-deoxy-, 3'-methyl-, 3'-methoxy, 3'-phosphate, 3'-aminolink, 3'-abasic amidite, or any other 3' modification groups. Those of ordinary skill in the art would be able to further contemplate other blocking agents for use as disclosed herein.

Any one or more of the ligation methods provided herein can be used in a ligation assay. Non-limiting example of ligation assays include a oligonucleotide ligation assay (OLA), a ligase chain reaction (LCR), a ligase detection reaction (LDR) and combination assays such as the OLA coupled with the polymerase chain reaction (PCR), e.g., OLA-PCR and PCR-OLA, the Combined Chain Reaction (CCR; a combination of PCR and LCR) and PCR-LDR (see, e.g., Landegren et al., Science 241:1077-80, 1988; Barany, Proc. Natl. Acad. Sci. 88:189-93, 1991; Grossman et al., Nucl. Acids Res. 22(21):4527-34, 1994; Bi and Stambrook, Nucl. Acids Res. 25(14):2949-51, 1997; Zirvi et al., Nucl. Acids Res., 27(24):e40, 1999; U.S. Pat. No. 4,988,617; and PCT Publication Nos. WO 97/31256 and WO 01/92579. Such assays have been used for single nucleotide polymorphism (SNP) analysis, SNP genotyping, mutation detection, identification of single copy genes, detecting microsatellite repeat sequences, and DNA adduct mapping, among other things. See also Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15-3-29 (1982); and Namsaraev, U.S. Pat. Pub. 2004/0110213. The fidelity of several known ligases, based on for example the evaluation of mismatch ligation or ligation rates, has been reported. For example, the NAD+-dependent ligase from the hyperthermophilic bacteria *Aquifex aeolicus* reportedly generates detectable 3' misligation products with C:A, T:G, and G:T mismatches (Tong et al., Nucl. Acids Res. 28(6):1447-54, 2000); a partially purified preparation of bovine DNA ligase III reportedly generated detectable 3' misligation products with C:T, G:T, and T:G mismatches, while human ligase I generated detectable 3' misligation products with C:T and G:T mismatches, but not T:G mismatches (Husain et al., J. Biol. Chem. 270(16):9683-90, 1995); and the DNA ligase from the thermophilic bacteria *Thermus thermophilus* (Tth) reportedly generates detectable levels of 3' misligation products with T:G and G:T mismatches (Luo et al., Nucl. Acids Res. 24(14):3071-78, 1996). Bacteriophage T4 DNA ligase reportedly generates detectable misligation products with a wide range of mismatched substrates and appears to have lower fidelity than *Thermus* species ligases by at least one to two orders of magnitude (Landegren et al., Science 241:1077-80, 1988; Tong et al., Nucl. Acids Res. 27(3):788-94, 1999).

A particularly useful assay is the oligonucleotide ligation assay (OLA). The OLA is a convenient, highly-stringent method that permits distinction among known DNA sequence variants (Landegren, 1988). For instance, multiplex analysis of highly polymorphic loci is useful for identification of individuals, e.g., for paternity testing and in forensic science, organ transplant donor-receiver matching, genetic disease diagnosis, prognosis, and pre-natal counseling, and other genetic-based testing which depend on the discrimination of single-base differences at a multiplicity of loci (Delahunty, 1996). Products of a multiplex OLA may be resolved electrophoretically from one another and from unligated probes under denaturing conditions with fluorescence detection (Grossman, 1994). For example, two PNA-DNA chimeras, a wild-type (WT) sequence chimera and a mutant sequence chimera, may bear different fluorescent dyes. Only when the mutant sequence is present in the target sample, will the mutant sequence chimera ligate to the adjacently annealed second probe (oligo) if the mutant base pair is at the ligation site. The ligation products may be discriminated by separation based on: (i) size using electrophoresis or chromatography and/or (ii) detectable labels (Grossman, 1994). With a plurality of fluorescent dyes labeled to chimeras with sequences targeting unique target sequences, multiplexed OLA can be conducted on a single sample in a single vessel. Requirements for efficient multiplex OLA include probes that anneal and ligate in a highly specific and rapid manner. The chimeras and second probe sequences may be selected such that the mutant base, or single base polymorphism, may be at the 5'-phosphate of the second probe or the 3'-terminus of the chimera. It is contemplated that OLA experiments of the present invention may be conducted on solid supports where the template nucleic acid, PNA-DNA chimeric probe, or the second probe may be immobilized on a solid particle or bead, or a solid porous or non-porous surface. When immobilized, the template, chimera or second probe is preferably covalently attached to the solid substrate, e.g. via a terminal monomer unit. The solid substrate may be polystyrene, controlled-pore-glass, silica gel, silica, polyacrylamide, magnetic beads, polyacrylate, hydroxyethylmethacrylate, polyamide, polyethylene, polyethyleneoxy, and copolymers and grafts of any of the above solid substrates. The configuration or format of the solid substrate may be small particles or beads of approximately 1 to 50 μm in diameter, membranes, frits, slides, plates, micromachined chips, alkanethiol-gold layers, non-porous surfaces, and polynucleotide-immobilizing media.

As described above, enzymatic ligation is typically accomplished using a ligase, which may be a polypeptide.

Suitable ligases include, for example, nucleic acid ligase, oligonucleotide ligase, DNA ligase, RNA ligase, and the like. Suitable RNA ligases include those described or used in, for example, any of U.S. Pat. Nos. 4,582,802; 5,665,545; 6,194,637; 6,444,429; 6,455,274; 6,576,453; 6,635,425; 6,855,523; 7,811,753; and the like, and/or any of U.S. Pat. Pubs. 2004/0171047A1, 2004/0191871A1, 2005/0266487A1, 2006/0223098A1, 2007/0037190A1, 2008/0160526A1; 2009/0061481A1, 2010/0099683A1, and/or 2010/0184618A1; and the like, all of which are incorporated by reference in their entirety into this application. Exemplary DNA ligases may include, for example, T3 DNA ligase, T4 DNA ligase, T5 DNA ligase, T7 DNA ligase, vaccinia virus DNA ligase, *E. coli* DNA ligase, mammalian DNA ligase I, mammalian DNA ligase II, mammalian DNA ligase III, Tth DNA ligase, KOD DNA ligase, a thermostable DNA ligase, and/or derivatives, fragments, and/or combinations thereof. Suitable RNA ligases include those described or used in, for example, any of U.S. Pat. Nos. 4,661,450; 5,516,664; 5,602,000; 5,807,674; 6,368,801; 6,492,161; 6,635,453; and the like, or any of U.S. Pat. Pub. Nos. 2003/0082536A1; 2004/0058330A1; 2005/0266439A1; 2005/0074774A1; 2008/0045418A1; 2010/00159526A1; and the like, all of which are incorporated by reference in their entirety into this application. Exemplary RNA ligases may include, for example, T4 RNA ligase, bacteriophage RB69 RNA ligase, *Autographa californica* nuclear polyhedrosis virus RNA ligase, a thermophilic RNA ligase, bacteriophage RM378 RNA ligase, bacteriophage TS2126 RNA ligase, and/or derivatives, fragments, and/or combinations thereof.

In some embodiments, the ligase is a "small footprint ligase" (SFL). A SFL has the the ability to ligate short polynucleotides (e.g., at least about 3 nucleotides). As described herein, a SFL may ligate oligonucleotides having a connector oligo length of as short as 3 base of hybridized DNA adjacent to 5'-phosphate hybridized DNA. In some embodiments, the SFL may be used to ligate oligonucleotides comprising short overlap sequences (e.g., short connector oligo length). For instance, the SFL may be used to ligate oligonucleotides of various nucleotides in length, whereby each oligo has at least a 3 nucleotide overlap with the splint oligo. Typical ligases would be better suited for ligating longer oligonucleotides (e.g., comprising 9 or more nucleotides; comprising 9, 10, 11, 12, 13, 14, 15, 20, 25, 30, etc nucleotides). In this way, oligonucleotide concentration may also be reduced to minimize chance of solution hybridization promoted non-antigen-binding ligation. For combining the ligation and PCR reaction into one step, ATP (cofactor for the ligase) can be omitted from the reaction mixture. In order to maintain the ligase function, the SFL may be pre-enriched with ATP prior to its purification and use.

A SFL may be a naturally occurring or non-naturally occurring (e.g., artificial, synthetic) ligase. A SFL can comprise a polypeptide sequence that is homologous to or a variant of a known ligase sequence or any portion thereof. Exemplary SFLs can have amino acid sequence identity of at least 70%, optionally at least 85%, optionally at least 90 or 95%, with a known ligase, and possesses one or more functional activities of a ligase. A SFL can thus comprise a polypeptide having any one or more of the following activities: (1) nucleophilic attack on ATP or $NAD^+$ resulting in release of PPi or NMN and formation of a covalent ligase-adenylate intermediate; (2) transferring the adenylate to the 5'-end of the 5'-phosphate-terminated DNA strand to form DNA-adenylate (e.g., the 5'-phosphate oxygen of the DNA strand attacks the phosphorus of ligase-adenylate); and, (3) formation of a covalent bond joining the polynucleotide termini and liberation of AMP (e.g., by the attack by the 3'-OH on DNA-adenylate). Optionally, the SFL can mediate any one or more of the following bond transformations: from phosphoanhydride (ATP) to phosphoramidate (ligase-adenylate); from phosphoramidate (ligase-adenylate) to phosphoanhydride (DNA-adenylate); and/or from phosphoanhydride (DNA-adenylate) to phosphodiester (sealed DNA). The SFL in one aspect is an enzyme that can mediate the formation of a covalent bond between two polynucleotide termini, e.g., a 3'-OH terminus and a 5'-$PO_4$ terminus are joined together to form a phosphodiester bond. In some instances, DNA ligation entails any one or more of three sequential nucleotidyl transfer steps, discussed below. All three chemical steps depend on a divalent cation cofactor. In one aspect, the SFL is an ATP-dependent ligase or a $NAD^+$-dependent ligase.

For example, the SFL can comprise any one or more domains characteristic of a ligase (e.g., an N-terminal nucleotidyltransferase (NTase) domain and/or a C-terminal OB domain). The OB domain optionally comprises a five-stranded antiparallel beta-barrel plus an alpha-helix. Within the NTase domain is an adenylate-binding pocket composed of the six peptide motifs that define the covalent NTase enzyme family of polynucleotide ligases. Optionally, the NTase domain can comprise any one or more of the ligase amino acid motifs I, III, IIIa, IV, and/or V, and preferably all six motifs. Motif I (e.g., KxDGxR or a "KXDG" motif) optionally contains a lysine. Exemplary sequences for each motif in CV ligase are ATPKIDGIR (motif I) (SEQ ID NO.: 1), SRT (motif Ia), EGSDGEIS (motif III) (SEQ ID NO.: 2), YWFDY (motif IIIa) (SEQ ID NO.: 3), EGVMIR (motif IV) (SEQ ID NO.: 4), LLKMK (motif V) (SEQ ID NO.:5). Motif 1 pfy contains a lysine residue. Other examples of motif I include CELKLDGLA (SEQ ID NO.: 6), VEHKVDGLS (SEQ ID NO.: 7), CEPKLDGLA (SEQ ID NO.: 8), CELKLDGVA (SEQ ID NO.: 9), AEIKYDGVR (SEQ ID NO.: 10), CEYKYDGQR (SEQ ID NO.: 11), VDYKYDGER (SEQ ID NO.: 12), FEIKYDGAR (SEQ ID NO.: 13), FEGKWDGYR (SEQ ID NO.: 14), AREKIHGTN (SEQ ID NO.: 15), ACEKVHGTN (SEQ ID NO.: 16), ILTKEDGSL (SEQ ID NO.: 17), and VEEKVDGYN (SEQ ID NO.: 18). Examples of motif Ia include TRG, SRT, SRR, SRN, SRS, KRT, KRS, SKG and TRG. Examples of motif III include LEVRGEVF (SEQ ID NO.: 19), VEVRGECY (SEQ ID NO.: 20), LEVRGEVY (SEQ ID NO.: 21), LEARGEAF (SEQ ID NO.: 22), FMLDGELM (SEQ ID NO.: 23), EGSDGEIS (SEQ ID NO.: 24), FILDTEAV (SEQ ID NO.: 25), FIIEGEIV (SEQ ID NO.: 26), AIVEGELV (SEQ ID NO.: 27), VVLDGEAV (SEQ ID NO.: 28), YQVFGEFA (SEQ ID NO.: 29), LVLNGELF (SEQ ID NO.: 30), FTANFEFV (SEQ ID NO.: 31) and LILVGEMA (SEQ ID NO.: 32). Examples of motif IIIa include FCYGV (SEQ ID NO.: 33), FLYTV (SEQ ID NO.: 34), TFYAL (SEQ ID NO.: 35), ICHGL (SEQ ID NO.: 36), NAYGI (SEQ ID NO.: 37), FVYGL (SEQ ID NO.: 38), KLYAI (SEQ ID NO.: 39), YWFDY (SEQ ID NO.: 40), YAFDI (SEQ ID NO.: 41), FLFDL (SEQ ID NO.: 42), NLFDV (SEQ ID NO.: 43), WAFDL (SEQ ID NO.: 44), YVFDI (SEQ ID NO.: 45), FAFDI (SEQ ID NO.: 46), ILLNA (SEQ ID NO.: 47), and FLFDV (SEQ ID NO.: 48). Examples of motif IV include DGVVIK (SEQ ID NO.: 49), DGIVIK (SEQ ID NO.: 50), DGVVK (SEQ ID NO.: 51), DGTVLK (SEQ ID NO.: 52), EGLIVK (SEQ ID NO.: 53), EGVMIR (SEQ ID NO.: 54), EGLMVK (SEQ ID NO.: 55), EGVMVK (SEQ ID NO.: 56), EGLMAK (SEQ ID NO.: 57), EGVIAK (SEQ ID NO.:

58), EGYVLK (SEQ ID NO.: 59), EGVVIR (SEQ ID NO.: 60), EGYVAV (SEQ ID NO.: 61), and EGIIMK (SEQ ID NO.: 62). Examples of motif V include AVAFK (SEQ ID NO.: 63), AIAYK (SEQ ID NO.: 64), ALAYK (SEQ ID NO.: 65), AIAYK (SEQ ID NO.: 66), WWKMK (SEQ ID NO.: 67), LLKMK (SEQ ID NO.: 68), WLKLK (SEQ ID NO.: 69), WIKLK (SEQ ID NO.: 70), WLKIK (SEQ ID NO.: 71), WVKDK (SEQ ID NO.: 72), AIKCK (SEQ ID NO.: 73), IIKLR (SEQ ID NO.: 74), HFKIK (SEQ ID NO.: 75) and IVKYV (SEQ ID NO.: 76). The SFL optionally comprises all six motifs. Optionally all six motifs are found together in a naturally-occurring ligase, such as a SFL identified herein. In some embodiments, the SFL is not an RNA-capping enzyme. The ligase optionally comprises any functional portion of a SFL. The ligase can be homologous to a SFL or any functional portion thereof, for example more than 75%, 85%, 90%, 95% or 99% homologous at the amino acid level. An exemplary SFL is a Chlorella virus DNA ligase (ChVLig) (Ho, et al., J Virol, 71(3):1931-19374 (1997)) or functional fragment or variant thereof. Representative examples of SFLs include CV ligase, DLX, DLXd, DLXd2 and MnM ligase. A preferred SFL is Chlorella Virus ligase. Some exemplary ligases are identified and their GI or accession numbers are provided in TABLE 1 below:

TABLE 1

| PRK08224 | | |
|---|---|---|
| B. Acidobacteria | | |
| Bacteria; Fibrobacteres/Acidobacteria group; Acidobacteria; unclassifed Acidobacteria; *Candidatus Koribacter*; *Candidatus Koribacter versatilis* | | |
| *Candidatus Solibacter usitatus* Ellin6076Candidatus Solibacter (1 proteins) | ATP-Dependent DNA Ligase | YP_826317 |
| C. Actinobacteria | | |
| Bacteria; Actinobacteria; Actinobacteria (class); Actinobacteridae; Actinomycetales; Corynebacterineae; Mycobacteriaceae; *Mycobacterium*; *Mycobacterium marinum* | | |
| *Mycobacterium gilvum* PYR-GCKMycobacterium (26 proteins) | ATP-Dependent DNA Ligase | YP_001132524 |
| *Mycobacterium vanbaalenii* PYR-1Mycobacterium (26 proteins) | ATP-Dependent DNA Ligase | YP_956315 |
| *Mycobacterium* sp. MCSMycobacterium (26 proteins) | ATP-Dependent DNA Ligase | YP_642076 |
| F. Chlamydiae/Verrucomicrobia | | |
| Bacteria; Chlamydiae/Verrucomicrobia group; Verrucomicrobia; Opitutae; Opitutales; Opitutaceae; *Opitutus*; *Opitutus terrae* | | |
| *Opitutus terrae* PB90-1Opitutus (1 proteins) | ATP-Dependent DNA Ligase | YP_001821013 |
| Organism | Protein name | Accession |
| PRK09125 | | |
| O. Betaproteobacteria | | |
| *Neisseria meningitidis* Z2491Neisseria (7 proteins) | DNA ligase | YP_002341892 |
| *Thiobacillus denitrificans* ATCC 25259Thiobacillus (1 proteins) | DNA ligase | YP_314570 |
| *Variovorax paradoxus* S110Variovorax (1 proteins) | DNA ligase | YP_002944627 |
| *Verminephrobacter eiseniae* EF01-2Verminephrobacter (1 proteins) | DNA ligase | YP_998235 |
| P. Deltaproteobacteria | | |
| *Desulfobacterium autotrophicum* HRM2Desulfobacterium (1 proteins) | LigA2 | YP_002604477 |
| *Myxococcus xanthus* DK 1622Myxococcus (1 proteins) | DNA ligase | YP_628883 |
| Q. Epsilonproteobacteria | | |
| *Campylobacter jejuni* subsp. *jejuni* NCTC 11168Campylobacter (10 proteins) | ATP-dependent DNA ligase | YP_002345037 |
| *Sulfurimonas denitrificans* DSM 1251Sulfurimonas (1 proteins) | DNA ligase | YP_393098 |
| R. Gammaproteobacteria | | |
| *Aggregatibacter aphrophilus* NJ8700Aggregatibacter (2 proteins) | ATP-dependent DNA ligase | YP_003007537 |
| *Haemophilus influenzae* PittEEHaemophilus (3 proteins) | ATP-dependent DNA ligase | YP_001290961 |
| *Shewanella baltica* OS195Shewanella (18 proteins) | ATP-dependent DNA ligase | YP_001554317 |

TABLE 1-continued

| | | |
|---|---|---|
| *Shewanella loihica* PV-4 Shewanella (18 proteins) | ATP-dependent DNA ligase | YP_001093713 |
| *Vibrio cholerae* M66-2 Vibrio (9 proteins) | DNA ligase | YP_002810248 |
| PHA0454 | | | b. Viruses

| | | |
|---|---|---|
| Viruses; dsDNA viruses, no RNA stage; Caudovirales; Podoviridae; Autographivirinae; phiKMV-like viruses | | |
| Pseudomonas phage LKD16 phiKMV-like viruses (7 proteins) | ATP-dependent DNA ligase | YP_001522807 |
| CLSZ2445448 | | | a. Eukaryota

| | | |
|---|---|---|
| Eukaryota; Alveolata; Ciliophora; Intramacronucleata; Oligohymenophorea; Peniculida; Parameciidae; *Paramecium; Paramecium tetraurelia* | | |
| *Paramecium tetraurelia* strain d4-2 Paramecium (5 proteins) | DNA ligase | XP_001347270 |
| PRK07636 | | |

J. Firmicutes

| | | |
|---|---|---|
| Bacteria; Firmicutes; Bacilli; Bacillales; Bacillaceae; *Bacillus; Bacillus clausii* | | |
| *Bacillus subtilis* subsp. *subtilis* str. 168 Bacillus | ATP-dependent DNA ligase | NP_389932 |
| Bacteria; Firmicutes; Bacilli; Bacillales; Bacillaceae; *Geobacillus* | | |
| *Geobacillus* sp. Y412MC10 Geobacillus | ATP dependent DNA ligase | YP_003240778 |
| CLSK2551528 | | |

J. Firmicutes

| | | |
|---|---|---|
| Bacteria; Firmicutes; Bacilli; Bacillales; Bacillaceae; *Geobacillus* | | |
| *Geobacillus* sp. Y412MC10 Geobacillus (1 proteins) | ATP dependent DNA ligase | YP_003245332 |
| CLSK2470953 | | |

C. Actinobacteria

| | | |
|---|---|---|
| Bacteria; Actinobacteria; Actinobacteria (class); Actinobacteridae; Actinomycetales; Micrococcineae; Micrococcaceae; *Arthrobacter; Arthrobacter chlorophenolicus* | | |
| *Arthrobacter chlorophenolicus* A6 (plasmid) *Arthrobacter* (2 proteins) | ATP dependent DNA ligase | YP_002478427 |
| CLSK2469924 | | |

J. Firmicutes

| | | |
|---|---|---|
| Bacteria; Firmicutes; Bacilli; Bacillales; Alicyclobacillaceae; *Alicyclobacillus; Alicyclobacillus acidocaldarius; Alicyclobacillus acidocaldarius* subsp. *acidocaldarius* | | |
| *Alicyclobacillus acidocaldarius* subsp. *acidocaldarius* DSM 446 Alicyclobacillus | ATP dependent DNA ligase | YP_003185050 |
| CLSK2340991 | | |

N. Alphaproteobacteria

| | | |
|---|---|---|
| Bacteria; Proteobacteria; Alphaproteobacteria; Caulobacterales; Caulobacteraceae; *Phenylobacterium; Phenylobacterium zucineum* | | |
| *Phenylobacterium zucineum* HLK1 (plasmid) *Phenylobacterium* (2 proteins) | ATP-dependent DNA ligase | YP_002128631 |

TABLE 1-continued

CLSK2333706

J. Firmicutes

Bacteria; Firmicutes; Clostridia; Clostridiales; Peptococcaceae; *Candidatus Desulforudis*; *Candidatus Desulforudis audaxviator*

| | | |
|---|---|---|
| *Candidatus Desulforudis audaxviator* MP104CCandidatus Desulforudis (1 proteins) | ATP dependent DNA ligase | YP_001716762 |

CLSK962101

C. Actinobacteria

Bacteria; Actinobacteria; Actinobacteria (class); Actinobacteridae; Actinomycetales; Micromonosporineae; Micromonosporaceae; *Salinispora*; *Salinispora arenicola*

| | | |
|---|---|---|
| *Salinispora arenicola* CNS-205Salinispora (2 proteins) | DNA polymerase LigD ligase region | YP_001539124 |
| *Salinispora tropica* CNB-440Salinispora (2 proteins) | ATP dependent DNA ligase | YP_001160776 |

CLSK915249

C. Actinobacteria See CLSK2303611 above
Bacteria; Actinobacteria; Actinobacteria (class); Actinobacteridae; Actinomycetales; Streptomycineae; Streptomycetaceae; *Streptomyces*; *Streptomyces coelicolor*

| | | |
|---|---|---|
| *Streptomyces avermitilis* MA-4680 (plasmid) *Streptomyces* (2 proteins) | putative ATP-dependint DNA ligase | NP_828839 |
| *Streptomyces* sp. HK1 (plasmid) *Streptomyces* (2 proteins) | putative ATP-dependent DNA ligase | YP_001661618 |

CLSK862724

A. Archaea

Archaea; Euryarchaeota; Archaeoglobi; Archaeoglobales; Archaeoglobaceae; *Archaeoglobus*; *Archaeoglobus fulgidus*

| | | |
|---|---|---|
| *Archaeoglobus fulgidus* DSM 4304Archaeoglobus (1 proteins) | DNA ligase, putative | NP_070553 |

J. Firmicutes

| | | |
|---|---|---|
| *Pelotomaculum thermopropionicum* SIPelotomaculum (1 proteins) | ATP-dependent DNA ligase | YP_001211793 |
| *Thermoanaerobacter pseudethanolicus* ATCC 33223Thermoanaerobacter (2 proteins) | ATP dependent DNA ligase | YP_001664477 |

CLSK820690

A. Archaea

Archaea; Euryarchaeota; environmental samples

| | | |
|---|---|---|
| uncultured methanogenic archaeon RC-Ienvironmental samples (1 proteins) | ATP-dependent DNA ligase | YP_686457 |

N. Alphaproteobacteria

Bacteria; Proteobacteria; Alphaproteobacteria; Rhizobiales; Bradyrhizobiaceae; *Bradyrhizobium*; *Bradyrhizobium japonicum*

| | | |
|---|---|---|
| *Bradyrhizobium japonicum* USDA 110Bradyrhizobium (2 proteins) | DNA ligase | NP_774671 |
| *Bradyrhizobium* sp. BTAilBradyrhizobium (2 proteins) | putative ATP-dependent DNA ligase | YP_001243518 |

CLSK808255

N. Alphaproteobacteria

Bacteria; Proteobacteria; Alphaproteobacteria; Rhizobiales; Rhizobiaceae; *Sinorhizobium/Ensifer* group; *Sinorhizobium*; *Sinorhizobium medicae*

| | | |
|---|---|---|
| *Sinorhizobium medicae* WSM419Sinorhizobium (2 proteins) | DNA polymerase LigD ligase region | YP_001326990 |
| *Sinorhizobium meliloti* 1021 (plasmid)*Sinorhizobium* (2 proteins) | putative ATP-dependent DNA ligase Protein | NP_437750 |

TABLE 1-continued

CLSK806855

N. Alphaproteobacteria

Bacteria; Proteobacteria; Alphaproteobacteria;
Rhizobiales; Rhizobiaceae; *Rhizobium/Agrobacterium*
group; *Agrobacterium*; *Agrobacterium tumefaciens*

| | | |
|---|---|---|
| *Agrobacterium tumefaciens* str. C58 (plasmid) *Agrobacterium* (3 proteins) | ATP-dependent DNA ligase | NP_396032 |
| *Rhizobium leguminosarum* bv. *trifolii* WSM1325 (plasmid) *Rhizobium* (10 proteins) | DNA polymerase LigD, ligase domain Protein | YP_002973496 |
| *Rhizobium leguminosarum* bv. *trifolii* WSM2304 (plasmid) *Rhizobium* (10 proteins) | DNA polymerase LigD, ligase domain Protein | YP_002278005 |

CLSK390680

N. Alphaproteobacteria

Bacteria; Proteobacteria; Alphaproteobacteria; Rhizobiales; Phyllobacteriaceae;
*Mesorhizobium*; *Mesorhizobium loti*

| | | |
|---|---|---|
| *Mesorhizobium loti* MAFF303099Mesorhizobium (3 proteins) | hypothetical protein | NP_108282 |

Additional exemplary SFLs may include, for example:

(SF DNA Ligase, GenBank ID AAC96909.1, from
*Paramecium bursaria Chlorella* virus 1)
(SEQ ID NO.: 77)
MAITKPLLAATLENIEDVQFPCLATPKIDGIRSVKQTQMLSRTF

KPIRNSVMNRLLTELLPEGSDGEISIEGATFQDTTSAVMTGHKM

YNAKFSYYWFDYVTDDPLKKYIDRVEDMKNYITVHPHILEHAQV

KIIPLIPVEINNITELLQYERDVLSKGFEGVMIRKPDGKYKFGR

STLKEGILLKMKQFKDAEATIISMTALFKNTNTKTKDNFGYSKR

STHKSGKVEEDVMGSIEVDYDGVVFSIGTGFDADQRRDFWQNKE

SYIGKMVKFKYFEMGSKDCPRFPVFIGIRHEEDR;

(MnM DNA Ligase, GenBank ID YP_333052.1,
from *Burkholderia pseudomallei* 1710b
(equivalent sequence to ABA50091))
(SEQ ID NO.: 78)
MSGVPYGFKPNLAATLTKPELIKFPVWASPKIDGIRCVFFGGVA

YSRSLKPIPNPVVQEFAKAYANLLEGLDGELTVGSPTDANCMQN

SMAVMSKAAAPDFTFHVFDWFHPAQAHIEFWQRSDVVEDRIVQF

YDRYPEVDIRAAPQVLCTSLAHLDTNEARWLADGYEGMMIRDHC

GRYKFGRSTEREGGLVKVKRFTDAEAIVIGFEEEMHNANEAKRD

ATGRTERSTSKAGLHGKGTLGALVVKNERGIVFNIGTGFTAAQR

ADYWANHPSLFGKMVKFKHFDHGTVDAPRHPVFIGFRHPEDM;

(Hin DNA Ligase, GenBank ID P44121, from
*Haemophilus influenza*)
(SEQ ID NO.: 79)
MKFYRTLLLFFASSFAFANSDLMLLHTYNNQPIEGWVMSEKLDG

VRGYWNGKQLLTRQGQRLSPPAYFIKDFPPPFAIDGELFSERNHF

EEISTITKSFKGDGWEKLKLYVFDVPDAEGNLFERLAKLKAHLL

EHPTTYIEIIEQIPVKDKTHLYQFLAQVENLQGEGVVVRNPNAP

YERKRSSQILKLKTARGEECTVIAHHKGKGQFENVMGALTCKNH

RGEFKIGSGFNLNERENPPPIGSVITYKYRGITNSGKPRFATYW

REKK;

(DLX DNA Ligase, artificial ligase derived
from Hin DNA ligase from *Haemophilus
influenza*)
(SEQ ID NO.: 80)
MKFYRTLLLFFASSFAFANSDLMLLHTYNNQPIEGWVMSEKLDG

VRGYWNGKQLLTRQGQRLSPPAYFIKDFPPPFAIDGELFSERNHF

EEISSITKSFKGDGWEKLKLYVFDVPDAEGNLFERLAKLKAHLL

EHPTTYIEIIEQIPVKDKTHLYQFLAQVENLQGEGVVVRNPNAP

YERKRSSQILKLKTARGEECTVIAHHKGKGQFENVMGALTCKNH

RGEFKIGSGFNLNERENPPPIGSVITYKYRGITNSGKPRFATYW

REKK;

(DLXd DNA Ligase, artificial ligase derived
from Hin DNA ligase from *Haemophilus
influenza*)
(SEQ ID NO.: 81)
MKFYRTLLLFFASSFAFANSDLMLLHTYNNQPIEGWVMSEKLDG

VRGYWNGKQLLTRQGQRLSPPAYFIKDFPPPFAIDGELFSERNHF

EEISSITKSFKGDGWEKLKLYVFDVPDAEGNLFERLAKLKAHLL

EHPTTYIEIIEQIPVKDKTHLYQFLAQVENLQGEGVVVRNPNAP

YERKRSSQILKLKTARDEECTVIAHHKGKGQFENVMGALTCKNH

RGEFKIGSGFNLNERENPPPIGSVITYKYRGITNSGKPRFATYW

REKK;,
and (DLXd2 DNA Ligase (Gammaproteobacteria,
*Haemophilus influenza*) (modified))
(SEQ ID NO.: 82)
MLLHTYNNQPIEGWVMSEKLDGVRGYWNGKQLLTRQGQRLSPPA

YFIKDFPPPFAIDGELFSERNHFEEISSITKSFKGDGWEKLKLYV

FDVPDAEGNLFERLAKLKAHLLEHPTTYIEIIEQIPVKDKTHLY

QFLAQVENLQGEGVVVRNPNAPYERKRSSQILKLKTARDEECTV

IAHHKGKGQFENVMGALTCKNHRGEFKIGSGFNLNERENPPPIG

SVITYKYRGITNSGKPRFATYWREKK.

As used herein, the terms "amplification", "nucleic acid amplification", or "amplifying" refer to the production of multiple copies of a nucleic acid template, or the production of multiple nucleic acid sequence copies that are complementary to the nucleic acid template. The amplification reaction may be a polymerase-mediated extension reaction such as, for example, a polymerase chain reaction (PCR). However, any of the known amplification reactions may be suitable for use as described herein. The term "amplifying" that typically refers to an "exponential" increase in target nucleic acid may be used herein to describe both linear and exponential increases in the numbers of a select target sequence of nucleic acid. The term "amplification reaction mixture" and/or "master mix" may refer to an aqueous solution comprising the various (some or all) reagents used to amplify a target nucleic acid. Such reactions may also be performed using solid supports (e.g., an array). The reactions may also be performed in single or multiplex format as desired by the user. These reactions typically include enzymes, aqueous buffers, salts, amplification primers, target nucleic acid, and nucleoside triphosphates. Depending upon the context, the mixture can be either a complete or incomplete amplification reaction mixture. The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR as the nucleic acid amplification reaction, it is expected that other types of nucleic acid amplification reactions, including both polymerase-mediated amplification reactions (such as HDA, RPA, and RCA), as well as ligase-mediated amplification reactions (such as LDR, LCR, and gap-versions of each), and combinations of nucleic acid amplification reactions such as LDR and PCR (see for example U.S. Pat. No. 6,797,470) may also be suitable. For example, in addition to those described elsewhere herein, various ligation-mediated reactions, where for example ligation probes are employed as opposed to PCR primers. Additional exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., WO 2006/081222), strand displacement (see, e.g., U.S. Pat. No. RE39007E), partial destruction of primer molecules (see, e.g., WO2006087574)), ligase chain reaction (LCR) (see, e.g., Wu, et al., Genomics 4: 560-569 (1990)), and/or Barany, et al. PNAS USA 88:189-193 (1991)), Qβ RNA replicase systems (see, e.g., WO/1994/016108), RNA transcription-based systems (e.g., TAS, 3SR), rolling circle amplification (RCA) (see, e.g., U.S. Pat. No. 5,854,033; U.S. Pub. No. 2004/265897; Lizardi et al. Nat. Genet. 19: 225-232 (1998); and/or Banér et al. Nucleic Acid Res., 26: 5073-5078 (1998)), and strand displacement amplification (SDA) (Little, et al. Clin Chem 45:777-784 (1999)), among others. These systems, along with the many other systems available to the skilled artisan, may be suitable for use in amplifying target nucleic acids for use as described herein.

"Amplification efficiency" may refer to any product that may be quantified to determine copy number (e.g., the term may refer to a PCR amplicon, an LCR ligation product, and/or similar product). Reactions may be compared by carrying out at least two separate amplification reactions, each reaction being carried out in the absence and presence, respectively, of a reagent and/or step and quantifying amplification that occurs in each reaction.

Also provided are methods for amplifying a nucleic acid using at least one polymerase, at least one primer, dNTPs, and ligating and amplifying the target nucleic acid. In some embodiments of such methods, at least one primer is utilized. In certain embodiments, a nucleic acid amplification reaction mixture(s) comprising at least one polymerase, dNTPs, and at least one primer is provided. In other embodiments, methods for using such mixture(s) are provided. Target nucleic acids may be amplified using any of a variety of reactions and systems. Exemplary methods for amplifying nucleic acids include, for example, polymerase-mediated extension reactions. For instance, the polymerase-mediated extension reaction can be the polymerase chain reaction (PCR). In other embodiments, the nucleic acid amplification reaction is a multiplex reaction. For instance, exemplary methods for amplifying and detecting nucleic acids suitable for use as described herein are commercially available as TaqMan® (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900, all of which are hereby incorporated herein by reference in their entirety). TaqMan® assays are typically carried out by performing nucleic acid amplification on a target polynucleotide using a nucleic acid polymerase having 5'-3' nuclease activity, a primer capable of hybridizing to said target polynucleotide, and an oligonucleotide probe capable of hybridizing to said target polynucleotide 3' relative to said primer. In some embodiments, the oligonucleotide probe includes a detectable label (e.g., a fluorescent reporter molecule) and a quencher molecule capable of quenching the fluorescence of said reporter molecule. In certain embodiments, the detectable label and quencher molecule are part of a single probe. As amplification proceeds, the polymerase digests the probe to separate the detectable label from the quencher molecule. The detectable label (e.g., fluorescence) can be monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

Another exemplary system suitable for use as described herein utilizes double-stranded probes in displacement hybridization methods (see, e.g., Morrison et al. Anal. Biochem., 18:231-244 (1989); and/or Li, et al. Nucleic Acids Res., 30(2,e5) (2002)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes may be used, each containing different detectable labels, such that multiple target nucleic acids may be queried in a single reaction.

Additional exemplary methods for amplifying and detecting target nucleic acids suitable for use as described herein involve "molecular beacons", which are single-stranded hairpin shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher dye that prevents the detectable label from emitting a single when the probe is in the closed loop shape (e.g., not bound to a target nucleic acid). Thus, in the presence of a complementary target, the "stem" portion of the beacon separates out resulting in the probe hybridizing to the target. Other types of molecular beacons are also known and may be suitable for use in the methods described herein. Molecular beacons may be used in a variety of assay systems. One such system is nucleic acid sequence-based amplification (NASBA®), a single step isothermal process for amplifying RNA to double stranded DNA without temperature cycling. A NASBA reaction typically requires avian myeloblastosis virus (AMV), reverse transcriptase (RT), T7 RNA polymerase, RNase H, and two oligonucleotide primers. After amplification, the amplified target nucleic acid may be detected using a molecular beacon. Other uses for molecular beacons are known in the art and would be suitable for use in the methods described herein.

The Scorpion system is another exemplary assay format that may be used in the methods described herein. Scorpion primers are bi-functional molecules in which a primer is covalently linked to the probe, along with a detectable label (e.g., a fluorophore) and a quencher. In the presence of a target nucleic acid, the detectable label and the quencher separate which leads to an increase in signal emitted from the detectable label. Typically, a primer used in the amplification reaction includes a probe element at the 5' end along with a "PCR blocker" element (e.g., a hexethylene glycol (HEG) monomer (Whitcombe, et al. Nat. Biotech. 17: 804-807 (1999)) at the start of the hairpin loop. The probe typically includes a self-complementary stem sequence with a detectable label at one end and a quencher at the other. In the initial amplification cycles (e.g., PCR), the primer hybridizes to the target and extension occurs due to the action of polymerase. The Scorpion system may be used to examine and identify point mutations using multiple probes that may be differently tagged to distinguish between the probes. Using PCR as an example, after one extension cycle is complete, the newly synthesized target region will be attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for molecular beacons are known in the art and would be suitable for use in the methods described herein.

The nucleic acid polymerases that may be employed in the disclosed nucleic acid amplification reactions may be any that function to carry out the desired reaction including, for example, a prokaryotic, fungal, viral, bacteriophage, plant, and/or eukaryotic nucleic acid polymerase. As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5' to 3' direction. Since DNA polymerase can only add a nucleotide onto a pre-existing 3'-OH group, to begin a DNA synthesis reaction, the DNA polymerase needs a primer to which it can add the first nucleotide. Suitable primers may comprise oligonucleotides of RNA or DNA, or chimeras thereof (e.g., RNA/DNA chimerical primers). The DNA polymerases may be a naturally occurring DNA polymerases or a variant of natural enzyme having the above-mentioned activity. For example, it may include a DNA polymerase having a strand displacement activity, a DNA polymerase lacking 5' to 3' exonuclease activity, a DNA polymerase having a reverse transcriptase activity, or a DNA polymerase having an endonuclease activity.

Suitable nucleic acid polymerases may also comprise holoenzymes, functional portions of the holoenzymes, chimeric polymerase, or any modified polymerase that can effectuate the synthesis of a nucleic acid molecule. Within this disclosure, a DNA polymerase may also include a polymerase, terminal transferase, reverse transcriptase, telomerase, and/or polynucleotide phosphorylase. Non-limiting examples of polymerases may include, for example, T7 DNA polymerase, eukaryotic mitochondrial DNA Polymerase γ, prokaryotic DNA polymerase I, II, III, IV, and/or V; eukaryotic polymerase α, β, γ, δ, ε, η, ζ, ι, and/or κ; $E.$ $coli$ DNA polymerase I; $E.$ $coli$ DNA polymerase III alpha and/or epsilon subunits; $E.$ $coli$ polymerase IV, $E.$ $coli$ polymerase V; $T.$ $aquaticus$ DNA polymerase I; $B.$ $stearothermophilus$ DNA polymerase I; Euryarchaeota polymerases; terminal deoxynucleotidyl transferase (TdT); $S.$ $cerevisiae$ polymerase 4; translesion synthesis polymerases; reverse transcriptase; and/or telomerase. Non-limiting examples of suitable thermostable DNA polymerases that may be used include Taq, Tfl, Pfu, and Vent™ DNA polymerases, any genetically engineered DNA polymerases, any having reduced or insignificant 3' to 5' exonuclease activity (e.g., SuperScript™ DNA polymerase), and/or genetically engineered DNA polymerases (e.g., those having the active site mutation F667Y or the equivalent of F667Y (e.g., in Tth), AmpliTaqFS, ThermoSequenase™), Terminator I, Terminator II, Terminator III, Terminator Gamma (all available from NEB), and/or any derivatives and fragments thereof. Other nucleic acid polymerases may also be suitable as would be understood by one of skill in the art.

In another aspect, the present disclosure provides reaction mixtures for amplifying a nucleic acid sequence of interest (e.g., a target sequence). In some embodiments, the reaction mixture may further comprise a signal-generating compound (SGC) and/or detectable label. The methods may also include one or more steps for detecting the SGC and/or detectable label to quantitate the amplified nucleic acid.

A SGC may be a substance that is itself detectable in an assay of choice, or capable of reacting to form a chemical or physical entity (e.g., a reaction product) that is detectable in an assay of choice. Representative examples of reaction products include precipitates, fluorescent signals, compounds having a color, and the like. Representative SGC include e.g., bioluminescent compounds (e.g., luciferase), fluorophores (e.g., below), bioluminescent and chemiluminescent compounds, radioisotopes (e.g., $^{131}$I, $^{125}$I, $^{14}$C, $^{3}$H, $^{35}$S, $^{32}$P and the like), enzymes (e.g., below), binding proteins (e.g., biotin, avidin, streptavidin and the like), magnetic particles, chemically reactive compounds (e.g., colored stains), labeled oligonucleotides; molecular probes (e.g., CY3, Research Organics, Inc.), and the like. Representative fluorophores include fluorescein isothiocyanate, succinyl fluorescein, rhodamine B, lissamine, 9,10-diphenlyanthracene, perylene, rubrene, pyrene and fluorescent derivatives thereof such as isocyanate, isothiocyanate, acid chloride or sulfonyl chloride, umbelliferone, rare earth chelates of lanthanides such as Europium (Eu) and the like. Representative SGC's useful in a signal generating conjugate include the enzymes in: IUB Class 1, especially 1.1.1 and 1.6 (e.g., alcohol dehydrogenase, glycerol dehydrogenase, lactate dehydrogenase, malate dehydrogenase, glucose-6-phosphate dehydrogenase, glyceraldehyde-3-phosphate dehydrogenase and the like); IUB Class 1.11.1 (e.g., catalase, peroxidase, amino acid oxidase, galactose oxidase, glucose oxidase, ascorbate oxidase, diaphorase, urease and the like); TUB Class 2, especially 2.7 and 2.7.1 (e.g., hexokinase and the like); IUB Class 3, especially 3.2.1 and 3.1.3 (e.g., alpha amylase, cellulase, β-galacturonidase, amyloglucosidase, β-glucuronidase, alkaline phosphatase, acid phosphatase and the like); TUB Class 4 (e.g., lyases); IUB Class 5 especially 5.3 and 5.4 (e.g., phosphoglucose isomerase, trios phosphatase isomerase, phosphoglucose mutase and the like.) SGCs may also generate products detectable by fluorescent and chemiluminescent wavelengths, e.g., sequencing dyes, luciferase, fluorescence emitting metals such as $^{152}$Eu, or others of the lanthanide series; compounds such as luminol, isoluminol, acridinium salts, and the like; bioluminescent compounds such as luciferin; fluorescent proteins (e.g., GFP or variants thereof); and the like. Attaching certain SGC to agents can be accomplished through metal chelating groups such as EDTA. The subject SGC shares the common property of allowing detection and/or quantification of an attached molecule. SGCs are optionally detectable using a visual or optical method; preferably, with a method amenable to automation such as a spectrophotometric method, a fluorescence method, a chemiluminescent method, an electrical nanometric method involving e.g., a change in conductance, impedance, resistance and the like and a magnetic field method. Some SGCs are optionally detectable with the naked eye or with a signal detection apparatus. Some SGCs are not themselves detectable but become detectable when subject to further treatment. The SGC can be attached in any manner (e.g., through covalent or non-covalent bonds) to a binding agent of interest (e.g., an antibody or a PDZ polypeptide). SGCs suitable for attachment to agents such as antibodies include colloidal gold, fluorescent antibodies, Europium, latex particles, and enzymes. The agents that bind to NS1 and NP can each comprise distinct SGCs. For example, red latex particles can be conjugated to anti-NS1 antibodies and blue latex particles can be conjugated to anti-NP antibodies. Other detectable SGCs suitable for use in a lateral flow format include any moiety that is detectable by spectroscopic, photochemical, biochemical, immunochemical, electrical, optical, chemical, or other means. For example, suitable SGCs include biotin for staining with labeled streptavidin conjugate, fluorescent dyes (e.g., fluorescein, Texas red, rhodamine, green fluorescent protein, and the like), radiolabels, enzymes (e.g., horseradish peroxidase, alkaline phosphatase and others commonly used in an ELISA), and colorimetric SGCs such as colloidal gold or colored glass or plastic (e.g., polystyrene, polypropylene, latex beads). Patents that described the use of such labels include U.S. Pat. Nos. 3,817,837; 3,850,752; 3,939,350; 3,996,345; 4,277,437; 4,275,149; and 4,366,241. See also Handbook of Fluorescent Probes and Research Chemicals (6th Ed., Molecular Probes, Inc., Eugene, Oreg.). Radiolabels can be detected using photographic film or scintillation counters, fluorescent markers can be detected using a photodetector to detect emitted light.

Similarly, the term "detectable label" may refer to any of a variety of signaling molecules indicative of amplification. For example, SYBR GREEN and other DNA-binding dyes are detectable labels. Such detectable labels may comprise or may be, for example, nucleic acid intercalating agents or non-intercalating agents. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent may produce a detectable signal directly or indirectly. The signal may be detectable directly using, for example, fluorescence and/or absorbance, or indirectly using, for example, any moiety or ligand that is detectably affected by proximity to double-stranded nucleic acid is suitable such as a substituted label moiety or binding ligand attached to the nucleic acid binding agent. It is typically necessary for the nucleic acid binding agent to produce a detectable signal when bound to a double-stranded nucleic acid that is distinguishable from the signal produced when that same agent is in solution or bound to a single-stranded nucleic acid. For example, intercalating agents such as ethidium bromide fluoresce more intensely when intercalated into double-stranded DNA than when bound to single-stranded DNA, RNA, or in solution (see, e.g., U.S. Pat. Nos. 5,994,056; 6,171,785; and/or 6,814,934). Similarly, actinomycin D fluoresces red fluorescence when bound to single-stranded nucleic acids, and green when bound to double-stranded nucleic acids. And in another example, the photoreactive psoralen 4-aminomethyle-4-5'8-trimethylpsoralen (AMT) has been reported to exhibit decreased absorption at long wavelengths and fluorescence upon intercalation into double-stranded DNA (Johnson et al. Photochem. & Photobiol., 33:785-791 (1981). For example, U.S. Pat. No. 4,257,774 describes the direct binding of fluorescent intercalators to DNA (e.g., ethidium salts, daunomycin, mepacrine and acridine orange, 4'6-diamidino-α-phenylindole). Non-intercalating agents (e.g., minor groove binders as described herein such as Hoechst 33258, distamycin, netropsin) may also be suitable for use. For example, Hoechst 33258 (Searle, et al. Nuc. Acids Res. 18(13):3753-3762 (1990)) exhibits altered fluorescence with an increasing amount of target. Minor groove binders are described in more detail elsewhere herein.

Other DNA binding dyes are available to one of skill in the art and may be used alone or in combination with other agents and/or components of an assay system. Exemplary DNA binding dyes may include, for example, acridines (e.g., acridine orange, acriflavine), actinomycin D (Jain, et al. J. Mol. Biol. 68:21 (1972)), anthramycin, BOBO™-1, BOBO™-3, BO-PRO™-1, cbromomycin, DAPI (Kapuseinski, et al. Nuc. Acids Res. 6(112): 3519 (1979)), daunomycin, distamycin (e.g., distamycin D), dyes described in U.S. Pat. No. 7,387,887, ellipticine, ethidium salts (e.g., ethidium bromide), fluorcoumanin, fluorescent intercalators as described in U.S. Pat. No. 4,257,774, GelStar® (Cambrex Bio Science Rockland Inc., Rockland, Me.), Hoechst 33258 (Searle and Embrey, 1990, Nuc. Acids Res. 18:3753-3762), Hoechst 33342, homidium, JO-PRO™-1, LIZ dyes, LO-PRO™-1, mepacrine, mithramycin, NED dyes, netropsin, 4'6-diamidino-α-phenylindole, proflavine, POPO™-1, POPO™-3, PO-PRO™-1, propidium iodide, ruthenium polypyridyls, S5, SYBR® Gold, SYBR® Green I (U.S. Pat. Nos. 5,436,134 and 5,658,751), SYBR® Green II, SYTOX blue, SYTOX green, SYTO® 43, SYTO® 44, SYTO® 45, SYTOX® Blue, TO-PRO®-1, SYTO® 11, SYTO® 13, SYTO® 15, SYTO® 16, SYTO® 20, SYTO® 23, thiazole orange (Aldrich Chemical Co., Milwaukee, Wis.), TOTO™-3, YO-PRO®-1, and YOYO®-3 (Molecular Probes, Inc., Eugene, Oreg.), among others. SYBR® Green I (see, e.g., U.S. Pat. Nos. 5,436,134; 5,658,751; and/or 6,569,927), for example, has been used to monitor a PCR reactions. Other DNA binding dyes may also be suitable as would be understood by one of skill in the art.

For use as described herein, one or more detectable labels and/or quenching agents may be attached to one or more primers and/or probes (e.g., detectable label). The detectable label may emit a signal when free or when bound to one of the target nucleic acids. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As mentioned above, in some embodiments the detectable label may be attached to a probe, which may be incorporated into a primer, or may otherwise bind to the amplified target nucleic acid (e.g., a detectable nucleic acid binding agent such as an intercalating or non-intercalating dye). When using more than one detectable label, each should differ in their spectral properties such that the labels may be distinguished from each other, or such that together the detectable labels emit a signal that is not emitted by either detectable label alone. Exemplary detectable labels include, for instance, a fluorescent dye or fluorophore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluoresceins (e.g., 5-carboxy-2,7-dichlorofluorescein; 5-Carboxyfluorescein (5-FAM); 5-HAT (Hydroxy Tryptamine); 5-Hydroxy Tryptamine (HAT); 6-JOE; 6-carboxyfluorescein (6-FAM); FITC; 6-carboxy-1,4-dichloro-2',7'-dichlorofluorescein (TET); 6-carboxy-1,4-dichloro-2',4',5',7'-tetrachlorofluorescein (HEX); 6-carboxy-4',5'-dichloro-2',7'-dimethoxyfluorescein (JOE); Alexa fluors (e.g., 350, 405, 430, 488, 500, 514, 532, 546, 555, 568, 594, 610, 633, 635, 647, 660, 680, 700, 750); BODIPY fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP. EGFP), blue fluorescent protein (e.g., BFP, EBFP, EBFP2, Azurite, mKalama1), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY FL/BODIPY FL, Fluorescein/QSY7 and QSY9), LysoTracker and LysoSensor (e.g., LysoTracker Blue DND-22, LysoTracker Blue-White DPX, LysoTracker Yellow HCK-123, LysoTracker Green DND-26, LysoTracker Red DND-99, LysoSensor Blue DND-167, LysoSensor Green DND-189, LysoSensor Green DND-153, LysoSensor Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B can C, Sulphorhodamine G Extra, TAMRA (6-carboxytetramethylrhodamine), Tetramethylrhodamine (TRITC), WT), Texas Red, Texas Red-X, VIC and other labels described in, e.g., U.S. Pub. No. 2009/0197254 (incorporated herein by reference in its entirety), among others as would be known to those of skill in the art. Other detectable labels may also be used (see, e.g., U.S. Pub. No. 2009/0197254 (incorporated herein by reference in its entirety)), as would be known to those of skill in the art. Any of these systems and detectable labels, as well as many others, may be used to detect amplified target nucleic acids.

Some detectable labels can be sequence-based (also referred to herein as a "locus-specific detectable label"), for example 5' nuclease probes. Such probes may comprise one or more detectable labels. Various detectable labels are known in the art, for example (TaqMan® probes described herein (See also U.S. Pat. No. 5,538,848 (incorporated herein by reference in its entirety)) various stem-loop molecular beacons (See, e.g., U.S. Pat. Nos. 6,103,476 and 5,925,517 and Tyagi and Kramer, 1996, Nature Biotechnology 14:303-308), stemless or linear beacons (See, e.g., WO 99/21881; U.S. Pat. No. 6,485,901), PNA Molecular Beacons™ (See, e.g., U.S. Pat. Nos. 6,355,421 and 6,593,091), linear PNA beacons (See, e.g., Kubista et al., 2001, SPIE 4264:53-58), non-FRET probes (See, e.g., U.S. Pat. No. 6,150,097), Sunrise®/Amplifluor® probes (U.S. Pat. No. 6,548,250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes (Svanvik, et al. Anal Biochem 281:26-35 (2001)), self-assembled nanoparticle probes, ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766: 769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161; QuantiProbes (www.qiagen.com), HyBeacons (French, et al. Mol. Cell. Probes 15:363-374 (2001)), displacement probes (Li, et al. Nucliec Acids Res. 30:e5 (2002)), HybProbes (Cardullo, et al. PNAS 85:8790-8794 (1988)), MGB Alert (www.nanogen.com), Q-PNA (Fiandaca, et al. Genome Res. 11:609-611 (2001)), Plexor (www.Promega.com), LUX primers (Nazarenko, et al. Nucleic Acids Res. 30:e37 (2002)), DzyNA primers (Todd, et al. Clin. Chem. 46:625-630 (2000)). Detectable labels can also comprise black hole quenchers (Biosearch), Iowa Black (IDT), QSY quencher (Molecular Probes), and Dabsyl and Dabcel sulfonate/carboxylate Quenchers (Epoch). Detectable labels can also comprise two probes, wherein for example a fluor is on one probe, and a quencher on the other, wherein hybridization of the two probes together on a target quenches the signal, or wherein hybridization on a target alters the signal signature via a change in fluorescence. Exemplary systems may also include FRET, salicylate/DTPA ligand systems (see, e.g., Oser et al. Angew. Chem. Int. Engl. 29(10):1167 (1990)), displacement hybridization, homologous probes, and/or assays described in EP 070685 and/or U.S. Pat. No. 6,238,927. Detectable labels can also comprise sulfonate derivatives of fluorescein dyes with $SO_3$ instead of the carboxylate group, phosphoramidite forms of fluorescein, phosphoramidite forms of CY5 (available for example from Amersham).

The terms "polypeptide," "peptide" and "protein" are used interchangeably herein to refer to a polymer of amino acid residues, or any variant or functional fragment thereof. The terms apply to amino acid polymers in which one or more amino acid residue is an artificial chemical mimetic of a corresponding naturally occurring amino acid, as well as to naturally occurring amino acid polymers and non-naturally occurring amino acid polymers. The term "amino acid" includes naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Variants of a given nucleotide sequence or polypeptide sequence are optionally conservatively modified variants. With respect to particular nucleic acid sequences, conservatively modified variants refers to those nucleic acids which encode identical or essentially identical amino acid sequences, or where the nucleic acid does not encode an amino acid sequence, to essentially identical sequences.

The term "antibody" or "antibodies" may include whole and/or fragments and/or derivatives of antibodies in unpurified or partially purified form (e.g., hybridoma supernatant, ascites, polyclonal antisera) or in purified form. A "purified" antibody may be one that is separated from at least about 50% of the proteins with which it is initially found (e.g., as part of a hybridoma supernatant or ascites preparation). Preferably, a purified antibody is separated from at least about 60%, 75%, 90%, or 95% of the proteins with which it is initially found. Suitable derivatives may include fragments (e.g., Fab, $Fab_2$ or single chain antibodies (Fv for example)), as are known in the art. The antibodies may be of any suitable origin or form including, for example, murine (e.g., produced by murine hybridoma cells), or expressed as humanized antibodies, chimeric antibodies, human antibodies, and the like. Methods of preparing and utilizing various types of antibodies are well-known to those of skill in the art and would be suitable for use (see, for example, Harlow, et al. Antibodies: A Laboratory Manual, Cold Spring Harbor Laboratory, 1988; Harlow, et al. Using Antibodies: A Laboratory Manual, Portable Protocol No. 1, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016).

In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (e.g., about −20° C. or −70° C.), in lyophilized form, or under normal refrigeration conditions (e.g., about 4° C.). When stored in liquid form, it is preferred that a suitable buffer such as Tris-buffered saline (TBS) or phosphate buffered saline (PBS) is utilized. Antibodies and their derivatives may be incorporated into compositions (e.g., attached to oligonucleotides) described herein for use in vitro or in vivo. Antibodies may also be modified for use by, for example, biotinylation. Other methods for making and using antibodies available to one of skill in the art may also be suitable for use.

The methods described herein may be useful for detecting and/or quantifying a variety of target nucleic acids from a test sample (e.g., biological sample). A target nucleic acid is any nucleic acid for which an assay system is designed to identify or detect as present (or not), and/or quantify in a test sample. Such nucleic acids may include, for example, those of infectious agents (e.g., virus, bacteria, parasite, and the like), a disease process such as cancer, diabetes, or the like, or to measure an immune response. Exemplary "test samples" include various types of samples, such as biological samples. Exemplary biological samples include, for instance, a bodily fluid (e.g., blood, saliva, spinal fluid), a tissue sample, a food (e.g., meat) or beverage (e.g., milk) product, or the like. Other examples of biological samples may include, whole blood, serum, plasma, urine, synovial fluid, saliva, cerebrospinal fluid, tissue infiltrate, cervical or vaginal exudate, pleural effusion, bronchioalveolar lavage fluid, gastric lavage fluid, small or large bowel contents, and swab specimens from various bodily orifices dispersed in a suitable medium. Expressed nucleic acids may include, for example, genes for which expression (or lack thereof) is associated with medical conditions such as infectious disease (e.g., bacterial, viral, fungal, protozoal infections) or cancer. The methods described herein may also be used to detect contaminants (e.g., bacteria, virus, fungus, and/or protozoan) in pharmaceutical, food, or beverage products. The methods described herein may be also be used to detect rare alleles in the presence of wild type alleles (e.g., one mutant allele in the presence of $10^6$-$10^9$ wild type alleles). The methods are useful to, for example, detect minimal residual disease (e.g., rare remaining cancer cells during remission, especially mutations in the p53 gene or other tumor suppressor genes previously identified within the tumors), and/or measure mutation load (e.g., the frequency of specific somatic mutations present in normal tissues, such as blood or urine).

Kits for performing the methods described herein are also provided. The kit may comprise one or more probes (e.g., antibody conjugated to an oligonucleotide) a pair of oligonucleotides for amplifying at least one target nucleic acid from a sample, a biocatalyst (e.g., DNA polymerase) and/or corresponding one or more probes labeled with a detectable label. The kit may also include samples containing predefined target nucleic acids to be used in control reactions. The kit may also optionally include stock solutions, buffers, enzymes, detectable labels or reagents required for detection, tubes, membranes, and the like that may be used to complete the amplification reaction. In some embodiments, multiple primer sets are included. Other embodiments of particular systems and kits are also contemplated which would be understood by one of skill in the art.

Those skilled in the art will recognize, or be able to ascertain using no more than routine experimentation, many equivalents to the specific embodiments of the invention described herein. The scope of the present invention is not intended to be limited to this Description.

Unless otherwise apparent from the context, any feature can be claimed in combination with any other, or be claimed as not present in combination with another feature. A feature can be any piece of information that can characterize an invention or can limit the scope of a claim, for example any variation, step, feature, property, composition, method, step, degree, level, component, material, substance, element, mode, variable, aspect, measure, amount, option, embodiment, clause, descriptive term, claim element or limitation.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Where necessary, ranges have been supplied, and those ranges are inclusive of all sub-ranges there between.

In this disclosure, the use of the singular can include the plural unless specifically stated otherwise or unless, as will be understood by one of skill in the art in light of the present disclosure, the singular is the only functional embodiment. Thus, for example, "a" may mean more than one, and "one embodiment" may mean that the description applies to multiple embodiments. The phrase "and/or" denotes a shorthand way of indicating that the specific combination is contemplated in combination and, separately, in the alternative.

It will be appreciated that there is an implied "about" prior to the temperatures, concentrations, times, etc. discussed in the present teachings, such that slight and insubstantial deviations are within the scope of the present teachings herein. Also, the use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the invention.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

Generally, features described herein are intended to be optional unless explicitly indicated to be necessary in the specification. Non-limiting examples of language indicating that a feature is regarded as optional in the specification include terms such as "variation," "where," "while," "when," "optionally," "include," "preferred," "especial," "recommended," "advisable," "particular," "should," "alternative," "typical," "representative," "various," "such as," "the like," "can," "may," "example," "embodiment," or "aspect," "in some," "example," "exemplary," "instance," "if" or any combination and/or variation of such terms.

"Isolated" or "purified" generally refers to isolation of a substance (compound, polynucleotide, protein, polypeptide, polypeptide composition) such that the substance comprises a significant percent (e.g., greater than 2%, greater than 5%, greater than 10%, greater than 20%, greater than 50%, or more, sometimes more than 90%, 95% or 99%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in a higher proportion than it is naturally found.

Sequence identity (also called homology) refers to similarity in sequence of two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (e.g., about 70% identity, preferably 75%, 80%, 85%, 90%, 95% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 90% identity at the amino acid level or at the nucleotide level. This definition also refers to the complement of a test sequence. Preferably, the identity exists over a region that is at least about 25, 50, or 100 residues in length, or across the entire length of at least one compared sequence. A preferred algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent conditions.

Any indication that a feature is optional is intended provide adequate support (e.g., under 35 U.S.C. 112 or Art. 83 and 84 of EPC) for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

Similarly, referents such as "a," "an," "said," or "the," are intended to support both single and/or plural occurrences unless the context indicates otherwise. For example "a dog" is intended to include support for one dog, no more than one dog, at least one dog, a plurality of dogs, etc. Non-limiting examples of qualifying terms that indicate singularity include "a single", "one," "alone," "only one," "not more than one," etc. Non-limiting examples of qualifying terms that indicate (potential or actual) plurality include "at least one," "one or more," "more than one," "two or more," "a multiplicity," "a plurality," "any combination of," "any permutation of," "any one or more of," etc. Claims or descriptions that include "or" between one or more members of a group are considered satisfied if one, more than one, or all of the group members are present in, employed in, or otherwise relevant to a given product or process unless indicated to the contrary or otherwise evident from the context.

In the claims, any active verb (or its gerund) is intended to indicate the corresponding actual or attempted action, even if no actual action occurs. For example, the verb "hybridize" and gerund form "hybridizing" and the like refer to actual hybridization or to attempted hybridization by contacting nucleic acid sequences under conditions suitable for hybridization, even if no actual hybridization occurs. Similarly, "detecting" and "detection" when used in the claims refer to actual detection or to attempted detection, even if no target is actually detected.

Furthermore, it is to be understood that the inventions encompass all variations, combinations, and permutations of any one or more features described herein. Any one or more features may be explicitly excluded from the claims even if the specific exclusion is not set forth explicitly herein. It should also be understood that disclosure of a reagent for use in a method is intended to be synonymous with (and provide support for) that method involving the use of that reagent, according either to the specific methods disclosed herein, or other methods known in the art unless one of ordinary skill in the art would understand otherwise. In addition, where the specification and/or claims disclose a method, any one or more of the reagents disclosed herein may be used in the method, unless one of ordinary skill in the art would understand otherwise.

All publications and patents cited in this specification are herein incorporated by reference in their entirety into this application as if each individual publication or patent were specifically and individually indicated to be incorporated by reference. Genbank records referenced by GID or accession number, particularly any polypeptide sequence, polynucleotide sequences or annotation thereof, are incorporated by reference herein. The citation of any publication is for its disclosure prior to the filing date and should not be construed as an admission that the present invention is not entitled to antedate such publication by virtue of prior invention.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Certain embodiments are further described in the following examples. These embodiments are provided as examples only and are not intended to limit the scope of the claims in any way.

EXAMPLES

Example 1

In an exemplary embodiment of typical proximity ligation assay (PLA) processes (FIG. 1), the probe mix (e.g., comprising two probes, A and B, (each probe comprising a streptavidin oligo "SAO" component and an antibody "Ab" component) in probe dilution buffer "PDB") and test sample (in sample dilution buffer "SDB") are combined into a binding reaction. Following the binding reaction (e.g., at 37° C. for 1 hour), the ligation reaction mixture is added in order to carry out the ligation reaction. To prepare the ligation reaction mixture, the ligase and ligation buffer are diluted. Following the ligation reaction (e.g., at 37° C. for 10 minutes), the ligated product is stabilized by protease digestion; the protease is then inactivated (e.g., using heat by incubation at 37° C. for 10 minutes followed by 95° C. for 5 minutes). Usually, a portion of the ligated product is transferred to the real-time PCR reaction mixture (comprising PCR primers and proximity probe mix "PCR-PP"), then placed on the PCR reaction plate in a qPCR instrument. Detection and quantification of the ligated product can then proceed using standard techniques.

A schematic of an exemplary improved PLA process is illustrated in FIG. 2. As shown therein, the binding reaction is the same as shown in FIG. 1. However, in some embodiments of the improved processes disclosed herein, as shown in FIG. 2, ligase is added to a real-time PCR mixture (comprising PCR primers, proximity probe and splint mix "PCR-PPS") which is then added directly to the binding reaction. In certain embodiments of the improved PLA processes, a test sample (e.g., cell lysate) is prepared, a binding reaction is allowed to take place and then a ligation buffer added directly thereto. To that mixture is then added a proximity probe mixture, and a PCR mixture. This combined reaction mixture is then incubated for a suitable amount of time (e.g., room temperature for 20 minutes and then 96° C. for 5 min) and PCR is performed. The PCR reaction mixture is then deposited onto the reaction plate in a qPCR instrument and detection and quantification of the ligated product can then proceed using standard techniques (as in typical PLA processes).

Example 2

Some exemplary embodiments of typical and improved PLA processes are also compared in FIGS. 3A and 3B. As shown in the embodiments illustrated therein, the typical process includes sample preparation, a binding reaction, ligation, ligase inactivation using a protease, protease inactivation (e.g., using heat), followed by real-time PCR. To carry out the PCR step, a portion of the reaction mixture containing the inactivated ligase and protease is transferred to the PCR plate, and the "PCR mix" (e.g., containing primers, dNTPs, polymerase, and the like) added thereto.

As shown in FIG. 3B, the improved process may eliminate the use of a protease and dilution of the reaction mixture prior to PCR. As shown therein, the ligase may be inactivated using heat, and the resultant reaction mixture placed directly into the qPCR assay. Thus, some embodiments of the improved PLA work flow uses entire binding reaction products in the real-time PCR well. This provides a simplified work-flow and reduced dilution of the reaction mixture. As a result, in some preferred embodiments of the improved PLA processes, the PCR reaction mixture contains a higher concentration of the ligated product (e.g., the target nucleic acid).

In order to reduce non-binding probe ligation, the probe concentration may be reduced. The splint (e.g., connector) oligo length and concentration may also be reduced to minimize chance of solution hybridization promoted by non-antigen-binding ligation (e.g., connector oligonucleotides of at least 14 bases in length (e.g., 9 bases overlapping a first oligo probe and 5 bases overlapping a second oligo probe (9+5)) vs. connector oligonucleotides of at least 18 bases in length (e.g., 9 bases overlapping a first oligo probe and 9 bases overlapping a second oligo probe (9+9)). In such embodiments, a small footprint ligase (SFL) may be used. As described herein, a SFL may ligate oligonucleotides having a connector oligo length of as short as 3 bases of hybridized DNA adjacent to 5'-phosphate hybridized DNA. For combining the ligation and PCR reaction into one step, in some embodiments, ATP (cofactor for the ligase) can be optionally omitted from the reaction mixture. In order to maintain the ligase function, in other embodiments, the SFL may be pre-enriched with ATP prior to its purification and use.

In some embodiments of the improved PLA processes splint oligos can be used that are either considered to be symmetrical splints or asymmetrical splints depending on the number of nucleotides that hybridize to each of the two oligo probes it is connecting. FIG. 4A and FIG. 4B diagrams asymmetrical and symmetrical splint types for use in the improved PLA processes as described herein. Asymmetrical splints (or "connectors") span across the two separate oligo probes (e.g., probe oligo A and B) with one of the ends of the splint (e.g., either the 3' end or the 5' end) having more nucleotides that hybridize to one of the probe oligos than the other end of the splint has nucleotides that hybridize to the alternative probe oligo (FIG. 4A). Symmetrical splints span across the two separate oligo probes (e.g., probe oligo A and B) with both ends of the splint (e.g., the 3' end and the 5' end) having equal number of nucleotides that hybridize to each of the two probe oligos (FIG. 4B).

Both asymmetrical and symmetrical splints can have any number of intervening nucleotides between each of its 3' and 5' ends that hybridize to the separate probe oligos. Alternatively, there may be no intervening nucleotides between each of the 3' and 5' ends that hybridize to the probe oligos.

Example 3

FIG. 5 provides a comparison between results obtained using exemplary embodiments of a typical process ("TaqMan® Protein Assay Open Kit from Life Technologies, Inc.; "PLA1") and an improved process (using methods disclosed herein; "PLA2"). Both assays were set up to target CSTB in NTera2 cell lysate. The binding reaction was identical for both PLA1 and PLA2 using the manufacturer's (Life Technologies, Inc.) recommended reagents and protocol in 4 µl volume binding reactions. After the binding reaction, PLA1 proceeded following the manufacturer's protocol and reagents. The PLA2 reaction was combined with 16 IA of ligation-PCR reaction mix. The ligation-PCR reaction mix consists of 10 µl the TaqMan® Protein Assay Fast Master Mix (Life Technologies, Inc.), 1 ul Universal PCR Assay and the connector oligonucleotide 9+5 and the SFL ligase, and 5 µl di-water. The ligation reaction was allowed to proceed for 10 minutes. The ligated product was then placed in a real-time PCR instrument (Step1Plus) and utilized according to the manufacturer's instructions.

As described above, in some embodiments, the improved process (PLA2) carries more target molecules into the PCR step (e.g., resulting in more amplicons being generated). The improvement provided thereby is shown in FIG. 5. As shown therein, the dCT of the improved process (PLA2) is much improved as compared to the typical process (PLA1). In this exemplary embodiment, the improved process provides at least about a one- to three-fold dCt improvement over the typical process.

The improved process also provides improved assay sensitivity. As shown by the exemplary embodiment in FIG. 6, the improved process provides about a two- to ten-fold increase in sensitivity over the typical process (FIG. 6). Sensitivity was calculated as the relative quantification (RQ) fold change using the results from the typical process as the calibrator. The dCt of the improved process was calculated as fold improvement over the typical process. Since the RQ is calculated from the dCt threshold of 2, and the fold-change is therefor indicative of the improvement in sensitivity. The data show that the sensitivity of the assay was improved by at least 2-fold, as determined using five different targets (GFP, hCSTB, hICAM1, hLIN28, and hOCT3/4). The GFP data was generated using the typical (e.g., PLA1) and improved (e.g., PLA2) processes as described above using a cell lysate into which rGFP was added (e.g., a "spiked-in" cell lysate) and a GFP probe used.

Example 4

In this example, two different splint lengths were tested at varying concentrations.

PLA experiments were carried out using typical PLA conditions ("TaqMan® Protein Assay Open Kit from Life Technologies, Inc.) according to the manufacturers instructions, using a T4 ligase, except that splint concentrations were varied within the range of 3.1 nM to 1000 nM. Splints were also designed to have a two different splint lengths of 18 (9+9; "99") or 16 (8+8; "88"). Cystatin B (CSTB) assay probes (from "TaqMan® Protein Expression Assay Kit (Human CSTB); Life Technologies, Inc.) were used to detect either 1000 pM or 0 pM (no protein control; "NPC") of recombinant CSTB protein in buffer. Ct values were plotted for each splint concentration and delta Ct values (NPC Ct values minus CSTB Ct values) and were plotted for each concentration used.

As shown in FIG. 7, a reduction in delta Ct was observed for the 99 splint at a low concentration of 3.1 nM as compared to higher concentrations used. There was also a delta Ct observed for the 88 splint at a concentration of 25 nM compared to higher concentrations. Collectively, these data demonstrate that ligated products are reduced when the splint length is decreased when the T4 ligase is used.

Example 5

In this example, five different splint lengths were tested using a single concentration.

PLA experiments were carried out using similar methods as described in Example 4, except that SF ligase instead of T4 ligase was used. Briefly, splints were designed to have a different splint lengths of 12 (3+9), 13 (4+9), 14 (5+9 or 7+7), 17 (8+9), or 18 (9+9). The concentration used for each of these splints was 100 nM. Raji lysate (Protein Expression Lysate Control Kit from Life Technologies, Inc.) was prepared at 500 cells/reaction or 0 cells/reaction ("NPC") and CSTB assay probes (from TaqMan® Protein Expression Assay Kit (Human CSTB); Life Technologies, Inc.) were used according to the manufacturer's instructions. Ct values were plotted for each splint type and delta Ct values (NPC Ct values minus 500 cell input Ct values) and were plotted for each.

As shown in FIG. 8, increasing dCT was observed for splints of 12 nucleotides in length up to 14 nucleotides in length (including both asymmetrical and symmetrical splint types). This demonstrates that SF ligase is capable of ligating both asymmetric and symmetric splints of both shorter and longer lengths.

Example 6

In this example, T4 ligase was compared to two different SF ligases (e.g., SF and DLxD).

PLA experiments were carried out using similar methods as described in Example 5, using the indicated ligases and splints of varying length, as indicated. Briefly, splints were designed to have a two different splint lengths of 14 (5+9; "95") or 18 (9+9; "99"). The concentration used for each of these splints was 100 nM. Raji lysate (Protein Expression Lysate Control Kit from Life Technologies, Inc.) was prepared at 500 cells/reaction or 0 cells/reaction ("NPC") and CSTB assay probes (from TaqMan® Protein Expression Assay Kit (Human CSTB); Life Technologies, Inc.) were used according to the manufacturer's instructions. Ct values were plotted for each ligase and splint type and delta Ct values (NPC Ct values minus 500 cell input Ct values) and were plotted for each.

As shown in FIG. 9, the T4 ligase resulted no noticeable dCt using the 5+9 splint. However, both SF ligases, SF and DLxD, were capable of ligating the target DNA using shorter splint types. In this experiment, SF used with the 5+9 splint resulted in the highest dCt.

The improved processes described herein, and exemplified throughout the Examples above, provide faster times from process start to results (fast), reduce hands-on time (simpler and cheaper), reduce lab plasticware usage (cheaper and greener), and increased signals and sensitivities. These improved processes provide simplified work flow by combining ligation and PCR steps, reduced dilution factor from binding to ligation step, reduced binding probe concentration to enable reduced dilution factor, use of shorter connector oligo to control background signal, use lower connector oligo concentration to control background signal, use of SF ligase to enable use of shorter connector oligo length, ATP enriched SF ligase purification scheme to omit ATP in ligation-PCR step, and enabling use of the entire reaction volume to improve the PLA signal and sensitivity.

While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A method for performing a proximity ligation assay on a test sample comprising:
   a) contacting a target protein or analyte with at least a first probe and a second probe, each probe having binding specificity for the protein or analyte, and being adjoined to at least one type of DNA oligonucleotide to form a binding reaction mixture;
   b) contacting the binding reaction mixture with a ligation-PCR reaction mixture comprising:
      (i) a small-footprint DNA ligase (SFL) selected from the group consisting of a ligase of SEQ ID NO.: 77, a ligase of SEQ ID NO.: 78, a ligase of SEQ ID NO.: 79, a ligase of SEQ ID NO.: 80, a ligase of SEQ ID NO.: 81, a ligase of SEQ ID NO.: 82, and combinations thereof;
      (ii) a splint oligonucleotide having a total length of less than 15 nucleotides, wherein said splint oligonucleotide is blocked at its 3'-end with a moiety that prevents polymerase activity;
      (iii) at least one primer; and
      (iv) a DNA polymerase,
   c) ligating the oligonucleotides on the first and second probes to one another to produce a target nucleic acid;
   d) amplifying the target nucleic acid; and
   e) detecting the amplified target nucleic acid, wherein the ligation and amplification steps occur in a single reaction mixture.

2. The method of claim 1, wherein at least one of said oligonucleotides on said first and second probes comprises at least three nucleotides.

3. The method of claim 1, wherein said oligonucleotides on said first and second probes, are at least partially complementary to one another.

4. The method of claim 1, wherein a portion of at least one of said probes is an antibody.

5. The method of claim 1, wherein a portion of each of said first and second probes are antibodies.

6. The method of claim 1, wherein the small footprint ligase is contacted with adenosine triphosphate (ATP) prior to use.

7. The method of claim 1, wherein adenosine triphosphate is omitted from the reaction mixture in step b) and wherein the SFL is contacted with adenosine triphosphate prior to use in step b).

8. The method of claim 1, wherein the ligated oligonucleotide is amplified using polymerase chain reaction (PCR).

9. The method claim 1, wherein said amplified ligated oligonucleotide is detected using quantitative PCR (qPCR).

10. The method of claim 1, wherein the 3' and 5' ends of the splint oligonucleotide are asymmetrical to one another.

11. The method of claim 1, wherein said ligase is inactivated after ligation using a protease or heat.

12. A method for detecting a target in a sample comprising:
- a) binding a first and a second probe, each of which binds specifically to the target, wherein each of the probes comprises a DNA oligonucleotide portion or tail;
- b) adding a mixture to the binding reaction of step (a), the mixture comprising:
    - (i) a small-footprint DNA ligase (SFL) selected from the group consisting of, a ligase of SEQ ID NO.: 77, a ligase of SEQ ID NO.: 78, a ligase of SEQ ID NO.: 79, a ligase of SEQ ID NO.: 80, a ligase of SEQ ID NO.: 81, a ligase of SEQ ID NO.: 82, and combinations thereof;
    - (ii) a splint oligonucleotide having a total length of less than 15 nucleotides, wherein said splint oligonucleotide is blocked at its 3'-end with a moiety that prevents polymerase activity;
    - (iii) at least one primer; and
    - (iv) a DNA polymerase,
- c) ligating the first and second oligonucleotide tails to produce a ligated oligonucleotide template; and
- d) performing a polymerase chain reaction (PCR) of the oligonucleotide template across the first and second oligonucleotide to quantify the said template, wherein steps c) and c) are performed in the same reaction mixture.

13. The method of claim 12, wherein the target is a protein or an analyte.

14. The method of claim 1, wherein said splint oligonucleotide is blocked with a 3'amino linker group.

15. The method of claim 12, wherein said splint oligonucleotide is blocked with a 3'amino linker group.

16. The method of claim 12, wherein the 3' and 5' ends of the splint oligonucleotide are asymmetrical to one another.

17. The method of claim 1, wherein the test sample comprises a cell lysate.

* * * * *

SEQUENCE LISTING

```
<160> NUMBER OF SEQ ID NOS: 84

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Thr Pro Lys Ile Asp Gly Ile Arg
1               5

<210> SEQ ID NO 2
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 2

Glu Gly Ser Asp Gly Glu Ile Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Trp Phe Asp Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Gly Val Met Ile Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Leu Lys Met Lys
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Glu Leu Lys Leu Asp Gly Leu Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Glu His Lys Val Asp Gly Leu Ser
1               5
```

```
<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Glu Pro Lys Leu Asp Gly Leu Ala
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Glu Leu Lys Leu Asp Gly Val Ala
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Glu Ile Lys Tyr Asp Gly Val Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Glu Tyr Lys Tyr Asp Gly Gln Arg
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Asp Tyr Lys Tyr Asp Gly Glu Arg
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Phe Glu Ile Lys Tyr Asp Gly Ala Arg
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Glu Gly Lys Trp Asp Gly Tyr Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Arg Glu Lys Ile His Gly Thr Asn
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Cys Glu Lys Val His Gly Thr Asn
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Leu Thr Lys Glu Asp Gly Ser Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Glu Glu Lys Val Asp Gly Tyr Asn
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Glu Val Arg Gly Glu Val Phe
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Glu Val Arg Gly Glu Cys Tyr
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Glu Val Arg Gly Glu Val Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Glu Ala Arg Gly Glu Ala Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Met Leu Asp Gly Glu Leu Met
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 24

Glu Gly Ser Asp Gly Glu Ile Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Phe Ile Leu Asp Thr Glu Ala Val
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Ile Ile Glu Gly Glu Ile Val
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ile Val Glu Gly Glu Leu Val
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Val Leu Asp Gly Glu Ala Val
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Gln Val Phe Gly Glu Phe Ala
1               5
```

```
<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Val Leu Asn Gly Glu Leu Phe
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Thr Ala Asn Phe Glu Phe Val
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Ile Leu Val Gly Glu Met Ala
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Cys Tyr Gly Val
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Leu Tyr Thr Val
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 35

Thr Phe Tyr Ala Leu
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Cys His Gly Leu
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asn Ala Tyr Gly Ile
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Val Tyr Gly Leu
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Leu Tyr Ala Ile
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Trp Phe Asp Tyr
1               5
```

```
<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Ala Phe Asp Ile
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Leu Phe Asp Leu
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asn Leu Phe Asp Val
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Ala Phe Asp Leu
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Val Phe Asp Ile
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 46

Phe Ala Phe Asp Ile
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Leu Leu Asn Ala
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Leu Phe Asp Val
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Gly Val Val Ile Lys
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Gly Ile Val Ile Lys
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Gly Val Val Val Lys
1               5
```

```
<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Gly Thr Val Leu Lys
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Gly Leu Ile Val Lys
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Gly Val Met Ile Arg
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Gly Leu Met Val Lys
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Gly Val Met Val Lys
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 57

Glu Gly Leu Met Ala Lys
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Gly Val Ile Ala Lys
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Gly Tyr Val Leu Lys
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Gly Val Val Ile Arg
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Gly Tyr Val Ala Val
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Gly Ile Ile Met Lys
1               5
```

```
<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Val Ala Phe Lys
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Ile Ala Tyr Lys
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Leu Ala Tyr Lys
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Ile Ala Tyr Lys
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Trp Trp Lys Met Lys
1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 68

Leu Leu Lys Met Lys
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Trp Leu Lys Leu Lys
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Trp Ile Lys Leu Lys
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Leu Lys Ile Lys
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Val Lys Asp Lys
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Ile Lys Cys Lys
1               5
```

-continued

```
<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Ile Lys Leu Arg
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

His Phe Lys Ile Lys
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Val Lys Tyr Val
1               5

<210> SEQ ID NO 77
<211> LENGTH: 298
<212> TYPE: PRT
<213> ORGANISM: Paramecium bursaria Chlorella virus 1

<400> SEQUENCE: 77

Met Ala Ile Thr Lys Pro Leu Leu Ala Ala Thr Leu Glu Asn Ile Glu
1               5                  10                  15

Asp Val Gln Phe Pro Cys Leu Ala Thr Pro Lys Ile Asp Gly Ile Arg
            20                  25                  30

Ser Val Lys Gln Thr Gln Met Leu Ser Arg Thr Phe Lys Pro Ile Arg
        35                  40                  45

Asn Ser Val Met Asn Arg Leu Leu Thr Glu Leu Leu Pro Glu Gly Ser
    50                  55                  60

Asp Gly Glu Ile Ser Ile Glu Gly Ala Thr Phe Gln Asp Thr Thr Ser
65                  70                  75                  80

Ala Val Met Thr Gly His Lys Met Tyr Asn Ala Lys Phe Ser Tyr Tyr
                85                  90                  95

Trp Phe Asp Tyr Val Thr Asp Pro Leu Lys Lys Tyr Ile Asp Arg
            100                 105                 110

Val Glu Asp Met Lys Asn Tyr Ile Thr Val His Pro His Ile Leu Glu
        115                 120                 125

His Ala Gln Val Lys Ile Ile Pro Leu Ile Pro Val Glu Ile Asn Asn
    130                 135                 140

Ile Thr Glu Leu Leu Gln Tyr Glu Arg Asp Val Leu Ser Lys Gly Phe
145                 150                 155                 160
```

```
Glu Gly Val Met Ile Arg Lys Pro Asp Gly Lys Tyr Lys Phe Gly Arg
                165                 170                 175

Ser Thr Leu Lys Glu Gly Ile Leu Leu Lys Met Lys Gln Phe Lys Asp
            180                 185                 190

Ala Glu Ala Thr Ile Ile Ser Met Thr Ala Leu Phe Lys Asn Thr Asn
        195                 200                 205

Thr Lys Thr Lys Asp Asn Phe Gly Tyr Ser Lys Arg Ser Thr His Lys
    210                 215                 220

Ser Gly Lys Val Glu Glu Asp Val Met Gly Ser Ile Glu Val Asp Tyr
225                 230                 235                 240

Asp Gly Val Val Phe Ser Ile Gly Thr Gly Phe Asp Ala Asp Gln Arg
                245                 250                 255

Arg Asp Phe Trp Gln Asn Lys Glu Ser Tyr Ile Gly Lys Met Val Lys
            260                 265                 270

Phe Lys Tyr Phe Glu Met Gly Ser Lys Asp Cys Pro Arg Phe Pro Val
        275                 280                 285

Phe Ile Gly Ile Arg His Glu Glu Asp Arg
    290                 295

<210> SEQ ID NO 78
<211> LENGTH: 306
<212> TYPE: PRT
<213> ORGANISM: Burkholderia pseudomallei

<400> SEQUENCE: 78

Met Ser Gly Val Pro Tyr Gly Phe Lys Pro Asn Leu Ala Ala Thr Leu
1               5                   10                  15

Thr Lys Pro Glu Leu Ile Lys Phe Pro Val Trp Ala Ser Pro Lys Ile
            20                  25                  30

Asp Gly Ile Arg Cys Val Phe Phe Gly Gly Val Ala Tyr Ser Arg Ser
        35                  40                  45

Leu Lys Pro Ile Pro Asn Pro Val Val Gln Glu Phe Ala Lys Ala Tyr
    50                  55                  60

Ala Asn Leu Leu Glu Gly Leu Asp Gly Glu Leu Thr Val Gly Ser Pro
65                  70                  75                  80

Thr Asp Ala Asn Cys Met Gln Asn Ser Met Ala Val Met Ser Lys Ala
                85                  90                  95

Ala Ala Pro Asp Phe Thr Phe His Val Phe Asp Trp Phe His Pro Ala
            100                 105                 110

Gln Ala His Ile Glu Phe Trp Gln Arg Ser Asp Val Val Glu Asp Arg
        115                 120                 125

Ile Val Gln Phe Tyr Asp Arg Tyr Pro Glu Val Asp Ile Arg Ala Ala
    130                 135                 140

Pro Gln Val Leu Cys Thr Ser Leu Ala His Leu Asp Thr Asn Glu Ala
145                 150                 155                 160

Arg Trp Leu Ala Asp Gly Tyr Glu Gly Met Met Ile Arg Asp His Cys
                165                 170                 175

Gly Arg Tyr Lys Phe Gly Arg Ser Thr Glu Arg Glu Gly Gly Leu Val
            180                 185                 190

Lys Val Lys Arg Phe Thr Asp Ala Glu Ala Ile Val Ile Gly Phe Glu
        195                 200                 205

Glu Glu Met His Asn Ala Asn Glu Ala Lys Arg Asp Ala Thr Gly Arg
    210                 215                 220

Thr Glu Arg Ser Thr Ser Lys Ala Gly Leu His Gly Lys Gly Thr Leu
225                 230                 235                 240
```

```
Gly Ala Leu Val Val Lys Asn Glu Arg Gly Ile Val Phe Asn Ile Gly
            245                 250                 255

Thr Gly Phe Thr Ala Ala Gln Arg Ala Asp Tyr Trp Ala Asn His Pro
        260                 265                 270

Ser Leu Phe Gly Lys Met Val Lys Phe Lys His Phe Asp His Gly Thr
        275                 280                 285

Val Asp Ala Pro Arg His Pro Val Phe Ile Gly Phe Arg His Pro Glu
        290                 295                 300

Asp Met
305

<210> SEQ ID NO 79
<211> LENGTH: 268
<212> TYPE: PRT
<213> ORGANISM: Haemophilus influenza

<400> SEQUENCE: 79

Met Lys Phe Tyr Arg Thr Leu Leu Leu Phe Ala Ser Ser Phe Ala
1               5                   10                  15

Phe Ala Asn Ser Asp Leu Met Leu Leu His Thr Tyr Asn Asn Gln Pro
            20                  25                  30

Ile Glu Gly Trp Val Met Ser Glu Lys Leu Asp Gly Val Arg Gly Tyr
        35                  40                  45

Trp Asn Gly Lys Gln Leu Leu Thr Arg Gln Gly Gln Arg Leu Ser Pro
    50                  55                  60

Pro Ala Tyr Phe Ile Lys Asp Phe Pro Pro Phe Ala Ile Asp Gly Glu
65                  70                  75                  80

Leu Phe Ser Glu Arg Asn His Phe Glu Glu Ile Ser Thr Ile Thr Lys
                85                  90                  95

Ser Phe Lys Gly Asp Gly Trp Glu Lys Leu Lys Leu Tyr Val Phe Asp
            100                 105                 110

Val Pro Asp Ala Glu Gly Asn Leu Phe Glu Arg Leu Ala Lys Leu Lys
        115                 120                 125

Ala His Leu Leu Glu His Pro Thr Thr Tyr Ile Glu Ile Ile Glu Gln
    130                 135                 140

Ile Pro Val Lys Asp Lys Thr His Leu Tyr Gln Phe Leu Ala Gln Val
145                 150                 155                 160

Glu Asn Leu Gln Gly Glu Gly Val Val Val Arg Asn Pro Asn Ala Pro
                165                 170                 175

Tyr Glu Arg Lys Arg Ser Ser Gln Ile Leu Lys Leu Lys Thr Ala Arg
            180                 185                 190

Gly Glu Glu Cys Thr Val Ile Ala His His Lys Gly Lys Gly Gln Phe
        195                 200                 205

Glu Asn Val Met Gly Ala Leu Thr Cys Lys Asn His Arg Gly Glu Phe
    210                 215                 220

Lys Ile Gly Ser Gly Phe Asn Leu Asn Glu Arg Glu Asn Pro Pro
225                 230                 235                 240

Ile Gly Ser Val Ile Thr Tyr Lys Tyr Arg Gly Ile Thr Asn Ser Gly
                245                 250                 255

Lys Pro Arg Phe Ala Thr Tyr Trp Arg Glu Lys Lys
            260                 265

<210> SEQ ID NO 80
<211> LENGTH: 268
<212> TYPE: PRT
<213> ORGANISM: Haemophilus influenza
```

<400> SEQUENCE: 80

Met Lys Phe Tyr Arg Thr Leu Leu Phe Phe Ala Ser Ser Phe Ala
1               5                   10                  15

Phe Ala Asn Ser Asp Leu Met Leu Leu His Thr Tyr Asn Asn Gln Pro
            20                  25                  30

Ile Glu Gly Trp Val Met Ser Glu Lys Leu Asp Gly Val Arg Gly Tyr
            35                  40                  45

Trp Asn Gly Lys Gln Leu Leu Thr Arg Gln Gly Gln Arg Leu Ser Pro
    50                  55                  60

Pro Ala Tyr Phe Ile Lys Asp Phe Pro Pro Phe Ala Ile Asp Gly Glu
65                  70                  75                  80

Leu Phe Ser Glu Arg Asn His Phe Glu Glu Ile Ser Ser Ile Thr Lys
                85                  90                  95

Ser Phe Lys Gly Asp Gly Trp Glu Lys Leu Lys Leu Tyr Val Phe Asp
            100                 105                 110

Val Pro Asp Ala Glu Gly Asn Leu Phe Glu Arg Leu Ala Lys Leu Lys
        115                 120                 125

Ala His Leu Leu Glu His Pro Thr Thr Tyr Ile Glu Ile Glu Gln
    130                 135                 140

Ile Pro Val Lys Asp Lys Thr His Leu Tyr Gln Phe Leu Ala Gln Val
145                 150                 155                 160

Glu Asn Leu Gln Gly Glu Gly Val Val Val Arg Asn Pro Asn Ala Pro
                165                 170                 175

Tyr Glu Arg Lys Arg Ser Ser Gln Ile Leu Lys Leu Lys Thr Ala Arg
            180                 185                 190

Gly Glu Glu Cys Thr Val Ile Ala His His Lys Gly Lys Gly Gln Phe
        195                 200                 205

Glu Asn Val Met Gly Ala Leu Thr Cys Lys Asn His Arg Gly Glu Phe
    210                 215                 220

Lys Ile Gly Ser Gly Phe Asn Leu Asn Glu Arg Glu Asn Pro Pro
225                 230                 235                 240

Ile Gly Ser Val Ile Thr Tyr Lys Tyr Arg Gly Ile Thr Asn Ser Gly
                245                 250                 255

Lys Pro Arg Phe Ala Thr Tyr Trp Arg Glu Lys Lys
            260                 265

<210> SEQ ID NO 81
<211> LENGTH: 268
<212> TYPE: PRT
<213> ORGANISM: Haemophilus influenza

<400> SEQUENCE: 81

Met Lys Phe Tyr Arg Thr Leu Leu Leu Phe Phe Ala Ser Ser Phe Ala
1               5                   10                  15

Phe Ala Asn Ser Asp Leu Met Leu Leu His Thr Tyr Asn Asn Gln Pro
            20                  25                  30

Ile Glu Gly Trp Val Met Ser Glu Lys Leu Asp Gly Val Arg Gly Tyr
            35                  40                  45

Trp Asn Gly Lys Gln Leu Leu Thr Arg Gln Gly Gln Arg Leu Ser Pro
    50                  55                  60

Pro Ala Tyr Phe Ile Lys Asp Phe Pro Pro Phe Ala Ile Asp Gly Glu
65                  70                  75                  80

Leu Phe Ser Glu Arg Asn His Phe Glu Glu Ile Ser Ser Ile Thr Lys
                85                  90                  95

```
Ser Phe Lys Gly Asp Gly Trp Glu Lys Leu Lys Leu Tyr Val Phe Asp
                100                 105                 110

Val Pro Asp Ala Glu Gly Asn Leu Phe Glu Arg Leu Ala Lys Leu Lys
            115                 120                 125

Ala His Leu Leu Glu His Pro Thr Thr Tyr Ile Glu Ile Ile Glu Gln
        130                 135                 140

Ile Pro Val Lys Asp Lys Thr His Leu Tyr Gln Phe Leu Ala Gln Val
145                 150                 155                 160

Glu Asn Leu Gln Gly Glu Gly Val Val Arg Asn Pro Asn Ala Pro
                165                 170                 175

Tyr Glu Arg Lys Arg Ser Ser Gln Ile Leu Lys Leu Lys Thr Ala Arg
                180                 185                 190

Asp Glu Glu Cys Thr Val Ile Ala His His Lys Gly Lys Gly Gln Phe
            195                 200                 205

Glu Asn Val Met Gly Ala Leu Thr Cys Lys Asn His Arg Gly Glu Phe
        210                 215                 220

Lys Ile Gly Ser Gly Phe Asn Leu Asn Glu Arg Glu Asn Pro Pro
225                 230                 235                 240

Ile Gly Ser Val Ile Thr Tyr Lys Tyr Arg Gly Ile Thr Asn Ser Gly
                245                 250                 255

Lys Pro Arg Phe Ala Thr Tyr Trp Arg Glu Lys Lys
                260                 265

<210> SEQ ID NO 82
<211> LENGTH: 246
<212> TYPE: PRT
<213> ORGANISM: Haemophilus influenza

<400> SEQUENCE: 82

Met Leu Leu His Thr Tyr Asn Asn Gln Pro Ile Glu Gly Trp Val Met
1               5                   10                  15

Ser Glu Lys Leu Asp Gly Val Arg Gly Tyr Trp Asn Gly Lys Gln Leu
            20                  25                  30

Leu Thr Arg Gln Gly Gln Arg Leu Ser Pro Pro Ala Tyr Phe Ile Lys
        35                  40                  45

Asp Phe Pro Pro Phe Ala Ile Asp Gly Glu Leu Phe Ser Glu Arg Asn
    50                  55                  60

His Phe Glu Glu Ile Ser Ser Ile Thr Lys Ser Phe Lys Gly Asp Gly
65                  70                  75                  80

Trp Glu Lys Leu Lys Leu Tyr Val Phe Asp Val Pro Asp Ala Glu Gly
                85                  90                  95

Asn Leu Phe Glu Arg Leu Ala Lys Leu Lys Ala His Leu Leu Glu His
            100                 105                 110

Pro Thr Thr Tyr Ile Glu Ile Ile Glu Gln Ile Pro Val Lys Asp Lys
        115                 120                 125

Thr His Leu Tyr Gln Phe Leu Ala Gln Val Glu Asn Leu Gln Gly Glu
    130                 135                 140

Gly Val Val Val Arg Asn Pro Asn Ala Pro Tyr Glu Arg Lys Arg Ser
145                 150                 155                 160

Ser Gln Ile Leu Lys Leu Lys Thr Ala Arg Asp Glu Glu Cys Thr Val
                165                 170                 175

Ile Ala His His Lys Gly Lys Gly Gln Phe Glu Asn Val Met Gly Ala
            180                 185                 190

Leu Thr Cys Lys Asn His Arg Gly Glu Phe Lys Ile Gly Ser Gly Phe
        195                 200                 205
```

```
Asn Leu Asn Glu Arg Glu Asn Pro Pro Pro Ile Gly Ser Val Ile Thr
    210                 215                 220

Tyr Lys Tyr Arg Gly Ile Thr Asn Ser Gly Lys Pro Arg Phe Ala Thr
225                 230                 235                 240

Tyr Trp Arg Glu Lys Lys
                245

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aaaaaaaaaa aa                                                              12

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 84

Lys Xaa Asp Gly Xaa Arg
1               5
```